(12) United States Patent
Wood et al.

(10) Patent No.: US 9,138,031 B2
(45) Date of Patent: Sep. 22, 2015

(54) METHOD OF MAKING A MECHANICAL FASTENING STRIP AND RETICULATED MECHANICAL FASTENING STRIP THEREFROM

(75) Inventors: Leigh E. Wood, Woodbury, MN (US); Thomas J. Gilbert, St. Paul, MN (US); Mark A. Peltier, Forest Lake, MN (US); Peter Kitzer, Echt (NL); Volker Hauschildt, Hilden (DE); Andreas Urban, Cologne (DE); William C. Unruh, Inver Grover Heights, MN (US); Kristopher K. Biegler, Minneapolis, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 87 days.

(21) Appl. No.: 13/028,912

(22) Filed: Feb. 16, 2011

(65) Prior Publication Data

US 2012/0204383 A1 Aug. 16, 2012

(51) Int. Cl.
*A44B 18/00* (2006.01)
*A61F 13/62* (2006.01)

(52) U.S. Cl.
CPC .......... *A44B 18/0069* (2013.01); *A44B 18/0046* (2013.01); *A61F 13/62* (2013.01); *Y10T 24/2708* (2015.01); *Y10T 24/2775* (2015.01)

(58) Field of Classification Search
CPC ........... A44B 18/0046; A44B 18/0061; A44B 18/0069; A61F 13/62; Y10T 24/2708; Y10T 24/2775
USPC .................................... 24/442, 445, 448, 452
See application file for complete search history.

(56) References Cited

U.S. PATENT DOCUMENTS

| 3,252,181 A | 5/1966 | Hureau |
| 3,522,637 A * | 8/1970 | Brumlik .......................... 24/445 |

(Continued)

FOREIGN PATENT DOCUMENTS

| DE | 102006038334 | 2/2008 |
| EP | 0191355 | 8/1986 |

(Continued)

OTHER PUBLICATIONS

U.S. Application entitled, "Mechanical Closure Element", filed Aug. 16, 2012, having U.S. Appl. No. 29/429,801.

(Continued)

*Primary Examiner* — Robert J Sandy
*Assistant Examiner* — David Upchurch

(57) ABSTRACT

A method of making a mechanical fastening strip and a reticulated mechanical fastening strip are disclosed. The method includes providing a backing having upstanding posts; providing interrupted slits through the backing, the interrupted slits being interrupted by at least one intact bridging region; spreading the slit backing to provide multiple strands separated from each other between at least some of the bridging regions to provide at least one opening; and fixing the multiple strands of the backing in a spread configuration. The reticulated mechanical fastening strip includes multiple strands of a backing attached to each other at bridging regions in the backing and separated from each other between the bridging regions to provide openings. Upstanding posts on each of the multiple strands have bases attached to the backing, and each of the multiple strands has a width that is greater than that of the bases of its attached upstanding posts.

19 Claims, 8 Drawing Sheets

(56) References Cited

U.S. PATENT DOCUMENTS

| | | | | |
|---|---|---|---|---|
| 3,645,433 | A | 2/1972 | Lucas | |
| 3,717,908 | A | 2/1973 | Perina | |
| 3,724,737 | A | 4/1973 | Bodnar | |
| 3,985,599 | A | 10/1976 | Lepoutre | |
| 3,985,600 | A | 10/1976 | Blais | |
| 4,001,366 | A * | 1/1977 | Brumlik | 264/147 |
| 4,152,479 | A | 5/1979 | Larsen | |
| 4,176,775 | A | 12/1979 | Brendemuehl | |
| 4,239,141 | A | 12/1980 | Frye | |
| 4,288,884 | A | 9/1981 | Bahls | |
| 4,294,240 | A | 10/1981 | Thill | |
| 4,560,372 | A | 12/1985 | Pieniak | |
| 4,568,344 | A | 2/1986 | Suzuki | |
| 4,676,784 | A | 6/1987 | Erdman | |
| 4,775,310 | A | 10/1988 | Fischer | |
| 4,842,794 | A | 6/1989 | Hovis et al. | |
| 4,894,060 | A * | 1/1990 | Nestegard | 604/391 |
| 4,925,080 | A | 5/1990 | Crouse | |
| 4,969,970 | A | 11/1990 | Suzuki | |
| 5,077,870 | A | 1/1992 | Melbye | |
| 5,133,112 | A * | 7/1992 | Gomez-Acevedo | 24/450 |
| 5,207,962 | A | 5/1993 | Hovis | |
| 5,256,231 | A | 10/1993 | Gorman | |
| 5,260,015 | A | 11/1993 | Kennedy | |
| 5,290,377 | A | 3/1994 | Aihara | |
| 5,300,058 | A | 4/1994 | Goulait | |
| 5,397,316 | A | 3/1995 | LaVon | |
| 5,419,695 | A | 5/1995 | Clegg | |
| 5,605,735 | A | 2/1997 | Zehner | |
| 5,611,790 | A | 3/1997 | Osborn, III | |
| 5,628,097 | A | 5/1997 | Benson | |
| 5,660,666 | A | 8/1997 | Dilnik | |
| 5,679,302 | A | 10/1997 | Miller | |
| 5,692,271 | A | 12/1997 | Provost | |
| 5,713,881 | A | 2/1998 | Rezai | |
| 5,722,127 | A * | 3/1998 | Coates | 24/304 |
| 5,776,343 | A | 7/1998 | Cullen et al. | |
| 5,845,375 | A | 12/1998 | Miller | |
| 5,860,194 | A * | 1/1999 | Takizawa et al. | 24/452 |
| 5,868,987 | A | 2/1999 | Kampfer | |
| 5,891,549 | A | 4/1999 | Beretta | |
| 5,897,546 | A * | 4/1999 | Kido et al. | 604/391 |
| 5,930,875 | A | 8/1999 | Schreiner | |
| 5,953,797 | A * | 9/1999 | Provost et al. | 24/452 |
| 6,030,373 | A | 2/2000 | VanGompel | |
| 6,039,911 | A | 3/2000 | Miller | |
| 6,054,091 | A | 4/2000 | Miller | |
| 6,075,179 | A * | 6/2000 | McCormack et al. | 604/367 |
| 6,093,870 | A | 7/2000 | Carlsson | |
| 6,132,660 | A | 10/2000 | Kampfer | |
| 6,146,369 | A | 11/2000 | Hartman | |
| 6,190,594 | B1 | 2/2001 | Gorman | |
| 6,190,758 | B1 * | 2/2001 | Stopper | 428/198 |
| 6,262,331 | B1 | 7/2001 | Nakahata | |
| 6,287,665 | B1 * | 9/2001 | Hammer | 428/100 |
| 6,419,667 | B1 | 7/2002 | Avalon | |
| 6,489,003 | B1 | 12/2002 | Levitt | |
| 6,575,953 | B2 | 6/2003 | Olson | |
| 6,588,073 | B1 | 7/2003 | Zoromski | |
| 6,627,133 | B1 * | 9/2003 | Tuma | 264/167 |
| 6,843,762 | B2 | 1/2005 | Munche | |
| 6,849,142 | B1 * | 2/2005 | Goulait | 156/62.4 |
| 6,994,698 | B2 | 2/2006 | Leak | |
| 7,001,475 | B2 | 2/2006 | Ausen | |
| 7,014,906 | B2 | 3/2006 | Tuman | |
| 7,032,278 | B2 * | 4/2006 | Kurtz, Jr. | 24/442 |
| 7,048,818 | B2 | 5/2006 | Krantz | |
| 7,048,984 | B2 * | 5/2006 | Seth et al. | 428/100 |
| 7,125,400 | B2 | 10/2006 | Igaue | |
| 7,198,743 | B2 * | 4/2007 | Tuma | 264/167 |
| 7,214,334 | B2 | 5/2007 | Jens | |
| 7,219,403 | B2 | 5/2007 | Miyamoto | |
| 7,223,314 | B2 * | 5/2007 | Provost | 156/259 |
| 7,241,483 | B2 * | 7/2007 | Ausen et al. | 428/100 |
| 7,371,302 | B2 | 5/2008 | Miyamoto | |
| 7,373,698 | B2 * | 5/2008 | Erdman et al. | 24/442 |
| 7,407,496 | B2 * | 8/2008 | Petersen | 604/390 |
| 7,444,722 | B2 | 11/2008 | McDaniel | |
| 7,670,522 | B2 | 3/2010 | Ausen | |
| 7,695,799 | B2 | 4/2010 | Cree | |
| 7,897,078 | B2 | 3/2011 | Petersen | |
| 8,020,262 | B2 | 9/2011 | Oertel | |
| 8,889,243 | B2 | 11/2014 | Hanschen | |
| 2002/0016581 | A1 | 2/2002 | Kline | |
| 2002/0112325 | A1 | 8/2002 | Keohan | |
| 2003/0008106 | A1 | 1/2003 | Guenther | |
| 2003/0087059 | A1 | 5/2003 | Jackson | |
| 2003/0130644 | A1 * | 7/2003 | Baker | 604/389 |
| 2003/0229326 | A1 | 12/2003 | Hovis et al. | |
| 2004/0147890 | A1 | 7/2004 | Nakahata | |
| 2004/0170801 | A1 | 9/2004 | Seth | |
| 2004/0261232 | A1 | 12/2004 | Kurtz, Jr. | |
| 2004/0261233 | A1 | 12/2004 | Kingsford | |
| 2005/0271858 | A1 * | 12/2005 | Ausen et al. | 428/100 |
| 2006/0288547 | A1 | 12/2006 | Jackson | |
| 2006/0293635 | A1 * | 12/2006 | Petersen | 604/385.03 |
| 2007/0035060 | A1 | 2/2007 | Harvey | |
| 2007/0039142 | A1 * | 2/2007 | Petersen et al. | 24/448 |
| 2007/0107571 | A1 | 5/2007 | Saeki | |
| 2007/0134489 | A1 | 6/2007 | Neugebauer | |
| 2008/0097368 | A1 * | 4/2008 | Molander | 604/391 |
| 2008/0281286 | A1 | 11/2008 | Petersen | |
| 2009/0217492 | A1 | 9/2009 | Gallant | |
| 2009/0311465 | A1 | 12/2009 | De Jong | |
| 2010/0025881 | A1 * | 2/2010 | Seth et al. | 264/145 |
| 2010/0100022 | A1 | 4/2010 | Greener | |
| 2010/0179463 | A1 | 7/2010 | Greener | |
| 2011/0147475 | A1 | 6/2011 | Biegler | |
| 2011/0151171 | A1 | 6/2011 | Biegler | |
| 2011/0313389 | A1 | 12/2011 | Wood | |
| 2012/0011685 | A1 | 1/2012 | Rocha | |
| 2012/0330266 | A1 | 12/2012 | Zonneveld | |
| 2014/0142533 | A1 | 5/2014 | Peltier | |
| 2014/0332999 | A1 | 11/2014 | Rothwell | |
| 2015/0096659 | A1 | 4/2015 | Gilbert | |
| 2015/0096660 | A1 | 4/2015 | Gilbert | |

FOREIGN PATENT DOCUMENTS

| | | |
|---|---|---|
| EP | 0341993 | 11/1989 |
| EP | 0539504 | 5/1993 |
| EP | 0755665 | 1/1997 |
| EP | 0941730 | 9/1999 |
| EP | 1066008 | 1/2001 |
| EP | 1641417 | 4/2006 |
| GB | 821959 | 10/1959 |
| GB | 1275541 | 5/1972 |
| GB | 2017485 | 10/1979 |
| JP | 2010-29532 | 2/2010 |
| WO | WO 94/02091 | 2/1994 |
| WO | WO 96/10481 | 4/1996 |
| WO | WO 00/50229 | 8/2000 |
| WO | WO 2004/077980 | 9/2004 |
| WO | WO 2005/122818 | 12/2005 |
| WO | WO 2011/163193 | 12/2011 |

OTHER PUBLICATIONS

U.S. Application entitled, "Mechanical Fastener", filed Aug. 16, 2012, having U.S. Appl. No. 29/429,799.

U.S. Application entitled, "Mechanical Fastening Nets and Methods of Making the Same", filed Aug. 16, 2012, having U.S. Appl. No. 13/587,655.

U.S. Application entitled, "Absorbent Article including Laminate and Method of Making the Same", filed Nov. 16, 2012, having U.S. Appl. No. 13/679,296.

International Search Report for PCT/US2012/025434, dated May 22, 2012, 7 pages.

US 5,389,416, 02/1995, Mody (withdrawn)

* cited by examiner

METHOD OF MAKING A MECHANICAL FASTENING STRIP AND RETICULATED MECHANICAL FASTENING STRIP THEREFROM

BACKGROUND

Hook and loop fastening systems, where the hook member typically includes a plurality of closely spaced upstanding projections with loop-engaging heads, and the loop member typically includes a plurality of woven, nonwoven, or knitted loops, are useful for providing releasable attachment in numerous applications. For example, hook and loop fastening systems are widely used in wearable disposable absorbent articles to fasten such articles around the body of a person. In typical configurations, a hook strip or patch on a fastening tab attached to the rear waist portion of a diaper or incontinence garment, for example, can fasten to a landing zone of loop material on the front waist region, or the hook strip or patch can fasten to the backsheet (e.g., nonwoven backsheet) of the diaper or incontinence garment in the front waist region. Hook and loop fasteners are also useful for disposable articles such as sanitary napkins. A sanitary napkin typically includes a back sheet that is intended to be placed adjacent to the wearer's undergarment. The back sheet may comprise hook fastener elements to securely attach the sanitary napkin to the undergarment, which mechanically engages with the hook fastener elements.

Some hook members have been made with openings in the backing from which the hooks project. See, e.g., U.S. Pat. No. 4,001,366 (Brumlik) and U.S. Pat. No. 7,407,496 (Peterson) and Int. Pat. Appl. Pub. Nos. WO 2005/122818 (Ausen et al.) and WO 1994/02091 (Hamilton).

SUMMARY

The present disclosure provides a mechanical fastening strip that comprises multiple strands of a thermoplastic backing attached to each other at bridging regions in the thermoplastic backing and separated from each other between at least some of the bridging regions. The present disclosure also provides a fastening laminate and absorbent article that comprise the mechanical fastening strip and methods of making the mechanical fastening strip.

In one aspect, the present disclosure provides a method of making a mechanical fastening strip. The method includes providing a thermoplastic backing having multiple rows of upstanding posts; slitting through the thermoplastic backing to provide a slit backing having interrupted slits between at least some pairs of adjacent rows of the upstanding posts, wherein each interrupted slit is interrupted by at least one intact bridging region of the slit backing; spreading the slit backing to provide multiple strands of the thermoplastic backing attached to each other at least at some of the bridging regions and separated from each other between at least some of the bridging regions to provide at least one opening; and fixing the multiple strands of the thermoplastic backing in a spread configuration to maintain the at least one opening between the multiple strands of the thermoplastic backing.

In another aspect, the method of making a mechanical fastening strip includes providing a thermoplastic backing having upstanding posts; slitting through the thermoplastic backing to provide a slit backing having interrupted slits, wherein each interrupted slit is interrupted by at least one intact bridging region of the slit backing; spreading the slit backing to provide multiple strands of the thermoplastic backing attached to each other at least at some of the bridging regions and separated from each other between at least some of the bridging regions to provide at least one opening; and annealing the multiple strands of the thermoplastic backing in a spread configuration to maintain the at least one opening between the multiple strands of the thermoplastic backing.

In another aspect, the present disclosure provides a mechanical fastening strip made according to any one of the aforementioned methods.

In another aspect, the present disclosure provides a reticulated mechanical fastening strip comprising:

multiple strands of a thermoplastic backing attached to each other at bridging regions in the thermoplastic backing and separated from each other between the bridging regions to provide openings in the mechanical fastening strip, each of the multiple strands having a longitudinal dimension, a width dimension, and a thickness; and a plurality of upstanding posts on each of the multiple strands, the upstanding posts having bases attached to the thermoplastic backing and caps distal from the thermoplastic backing, wherein the width dimension of each of the multiple strands is wider than at least the bases of the upstanding posts.

The mechanical fastening strip, for example, the reticulated mechanical fastening strip, according to and/or made according to the present disclosure has a unique and attractive appearance, which may be further enhanced by adding a color (e.g., a pigment) to the thermoplastic or to a carrier to which the mechanical fastening strip is attached. Furthermore, the openings in the mechanical fastening strip can provide breathability and flexibility to the mechanical fastening strip, which may enhance the comfort of the wearer, for example, of an absorbent article comprising the mechanical fastening strip disclosed herein.

The mechanical fastening strip, for example, the reticulated mechanical fastening strip, according to and/or made according to the present disclosure is able to cover a relatively large area with a relative small amount of material, which may lower the cost of the mechanical fastening strip. The methods disclosed herein allow openings to be provided in the mechanical fastening strip to achieve the aforementioned advantages without wasteful material loss. Also, because of the large area that may be covered by the mechanical fastening strip in an absorbent article, the mechanical fastening strip may resist shifting forces such as torsional or rotational forces caused by movement of the wearer of the absorbent article.

In this application, terms such as "a", "an" and "the" are not intended to refer to only a singular entity, but include the general class of which a specific example may be used for illustration. The terms "a", "an", and "the" are used interchangeably with the term "at least one". The phrases "at least one of" and "comprises at least one of" followed by a list refers to any one of the items in the list and any combination of two or more items in the list. All numerical ranges are inclusive of their endpoints and non-integral values between the endpoints unless otherwise stated.

The terms "first" and "second" are used in this disclosure. It will be understood that, unless otherwise noted, those terms are used in their relative sense only. In particular, in some embodiments certain components may be present in interchangeable and/or identical multiples (e.g., pairs). For these components, the designation of "first" and "second" may be applied to the components merely as a matter of convenience in the description of one or more of the embodiments.

The term "row" refers to hook elements lined up in a particular direction. The row or line of hook elements may be substantially straight. When an interrupted slit is cut between adjacent rows of hook elements, it means that the particular slit does not cross over a row of hook elements.

When it is said that an interrupted slit "extends" in a particular direction, it is meant that the slit is arranged or aligned in that direction or at least predominantly in that direction. The slit may be linear. As used herein a "linear" slit can be defined by two points in a line between two rows of upstanding posts. The slit may also be substantially linear, which means that the slit can have a slight curvature or slight oscillation. Some oscillation or curvature may result, for example, from the process of slitting a continuous web as would be understood by a person skilled in the art. Any oscillation or curvature is such that the slit generally does not have a portion that crosses over a row of upstanding posts. The slit may also have a wavy or sawtooth pattern with a small amplitude such that the pattern generally does not cross over a row of upstanding posts.

A slit that is cut "through" the backing means that the slit cuts through the entire thickness of the backing.

The terms "multiple" and "a plurality" refer to more than one.

The upstanding posts described herein include male fastening elements with or without loop-engaging heads that have an overhang. The term "loop-engaging" as used herein relates to the ability of a male fastening element to be mechanically attached to a loop material. Generally, male fastening elements with loop-engaging heads have a head shape that is different from the shape of the stem. For example, the male fastening element may be in the shape of a mushroom (e.g., with a circular or oval head enlarged with respect to the stem), a hook, a palm-tree, a nail, a T, or a J. The loop-engageability of male fastening elements may be determined and defined by using standard woven, nonwoven, or knit materials. A region of male fastening elements with loop-engaging heads generally will provide, in combination with a loop material, at least one of a higher peel strength, higher dynamic shear strength, or higher dynamic friction than a region of stems without loop-engaging heads. Male fastening elements that have "loop-engaging overhangs" or "loop-engaging heads" do not include ribs that are precursors to hook elements (e.g., elongate ribs that are profile extruded and subsequently cut to form male fastening elements upon stretching in the direction of the ribs). Such ribs would not be able to engage loops before they are cut and stretched. Typically, male fastening elements that have loop-engaging heads have a maximum thickness dimension of up to about 1 (in some embodiments, 0.9, 0.8, 0.7, 0.6, 0.5, or 0.45) millimeter.

The term "machine direction" (MD) as used above and below denotes the direction of a running, continuous web of the backing during the manufacturing of the mechanical fastening strip. When a mechanical fastening strip is cut into smaller portions from a continuous web, the machine direction corresponds to the length "L" of the hook strip. As used herein, the terms machine direction and longitudinal direction are typically used interchangeably. The term "cross-direction" (CD) as used above and below denotes the direction which is essentially perpendicular to the machine direction. When a mechanical fastening strip is cut into smaller portions from a continuous web, the cross direction corresponds to the width "W" of the hook strip.

For some embodiments, slits (e.g., partial slits) are said to penetrate the thickness of the backing in a certain percent range. The percent penetration may be calculated as depth of the slit divided by the thickness of the backing, with the quotient multiplied by 100.

The term "nonwoven" when referring to a sheet or web means having a structure of individual fibers or threads which are interlaid, but not in an identifiable manner as in a knitted fabric. Nonwoven fabrics or webs can be formed from various processes such as meltblowing processes, spunbonding processes, spunlacing processes, and bonded carded web processes.

The term "elastic" refers to any material that exhibits recovery from stretching or deformation. Likewise, the term "nonelastic" refers to any material that does not exhibit recovery from stretching or deformation.

"Elongation" in terms of percent refers to {(the extended length–the initial length)/the initial length} multiplied by 100.

The term "surface-bonded" when referring to the bonding of fibrous materials means that parts of fiber surfaces of at least portions of fibers are melt-bonded to the second surface of the backing, in such a manner as to substantially preserve the original (pre-bonded) shape of the second surface of the backing, and to substantially preserve at least some portions of the second surface of the backing in an exposed condition, in the surface-bonded area. Quantitatively, surface-bonded fibers may be distinguished from embedded fibers in that at least about 65% of the surface area of the surface-bonded fiber is visible above the second surface of the backing in the bonded portion of the fiber. Inspection from more than one angle may be necessary to visualize the entirety of the surface area of the fiber.

The term "loft-retaining bond" when referring to the bonding of fibrous materials means a bonded fibrous material comprises a loft that is at least 80% of the loft exhibited by the material prior to, or in the absence of, the bonding process. The loft of a fibrous material as used herein is the ratio of the total volume occupied by the web (including fibers as well as interstitial spaces of the material that are not occupied by fibers) to the volume occupied by the material of the fibers alone. If only a portion of a fibrous web has the second surface of the backing bonded thereto, the retained loft can be easily ascertained by comparing the loft of the fibrous web in the bonded area to that of the web in an unbonded area. It may be convenient in some circumstances to compare the loft of the bonded web to that of a sample of the same web before being bonded, for example, if the entirety of fibrous web has the second surface of the backing bonded thereto.

The above summary of the present disclosure is not intended to describe each disclosed embodiment or every implementation of the present disclosure. The description that follows more particularly exemplifies illustrative embodiments. It is to be understood, therefore, that the drawings and following description are for illustration purposes only and should not be read in a manner that would unduly limit the scope of this disclosure.

BRIEF DESCRIPTION OF THE DRAWINGS

The disclosure may be more completely understood in consideration of the following detailed description of various embodiments of the disclosure in connection with the accompanying drawings, in which.

DETAILED DESCRIPTION

Figure 1A:
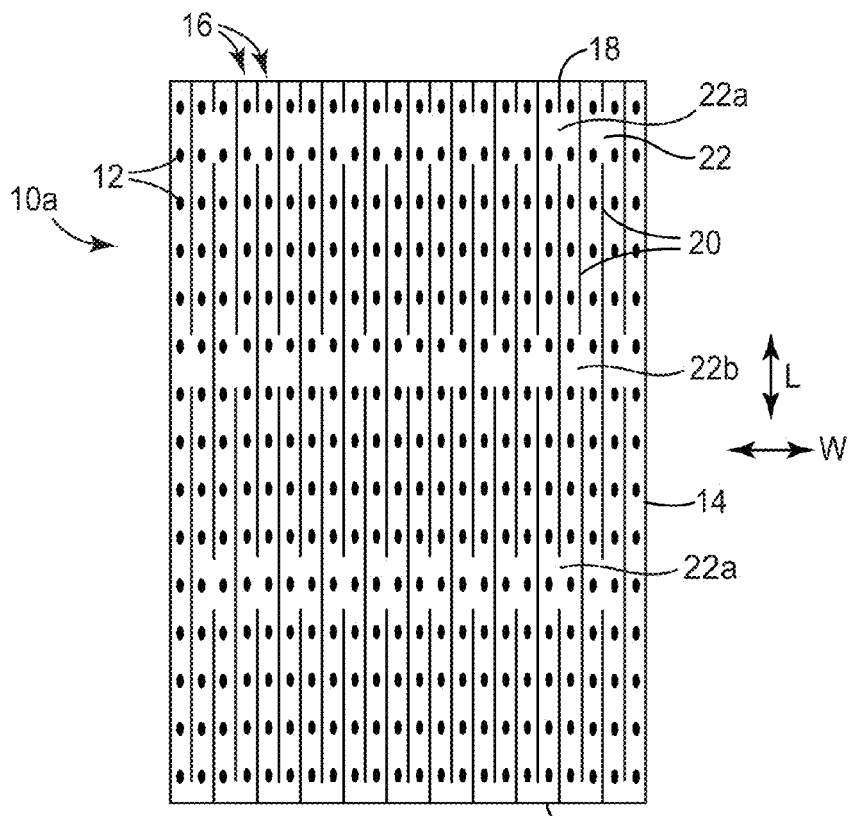
FIG. 1A is a top view of an exemplary backing having upstanding posts and interrupted slits through the backing, useful for the methods of making a mechanical fastening strip disclosed herein.

Reference will now be made in detail to embodiments of the disclosure, one or more examples of which are illustrated in the drawings. Features illustrated or described as part of one embodiment can be used with other embodiments to yield still a third embodiment. It is intended that the present disclosure include these and other modifications and variations.

FIG. 1A illustrates an exemplary slit backing 10a having upstanding posts 12 and interrupted slits 20 through the backing, useful for the methods of making a mechanical fastening strip according to some embodiments of the present disclosure. Slit backing 10a, which can be a mechanical fastening strip, has a thermoplastic backing 14 with multiple rows 16 of upstanding posts 12 projecting from a first surface of the backing 14.

The first surface of the backing is the surface that is visible in FIG. 1A. The first surface can also be called the first major surface in any of the embodiments disclosed herein. In the illustrated embodiment, the multiple rows 16 of upstanding posts 12 are aligned in the longitudinal direction L. Interrupted slits 20 are cut into the backing between some pairs of adjacent rows 16 of upstanding posts 12. It should be understood generally that when slits are cut between at least some pairs of adjacent rows 16, there are at least two slits in the backing 14. The illustrated interrupted slits 20 are linear in the same direction "L" as the multiple rows 16 and extend from the top edge 18 to the bottom edge 28 of the backing 14. The interrupted slits are interrupted by intact bridging regions 22 of the backing 14. The bridging regions 22 are regions where the backing is not cut through, and at least a portion of the bridging regions can be considered collinear with interrupted slit 20. In the illustrated embodiment, the interrupted slits 20 are evenly spaced among the rows of upstanding posts 12 although this is not a requirement. Further, in the illustrated embodiment, the bridging regions 22 are staggered in a direction "W" perpendicular to the direction "L" of the interrupted slits 20. The bridging regions 22a and 22b are staggered such that bridging region 22b is located substantially midway between bridging regions 22a in the direction "L".

Figure 1B:
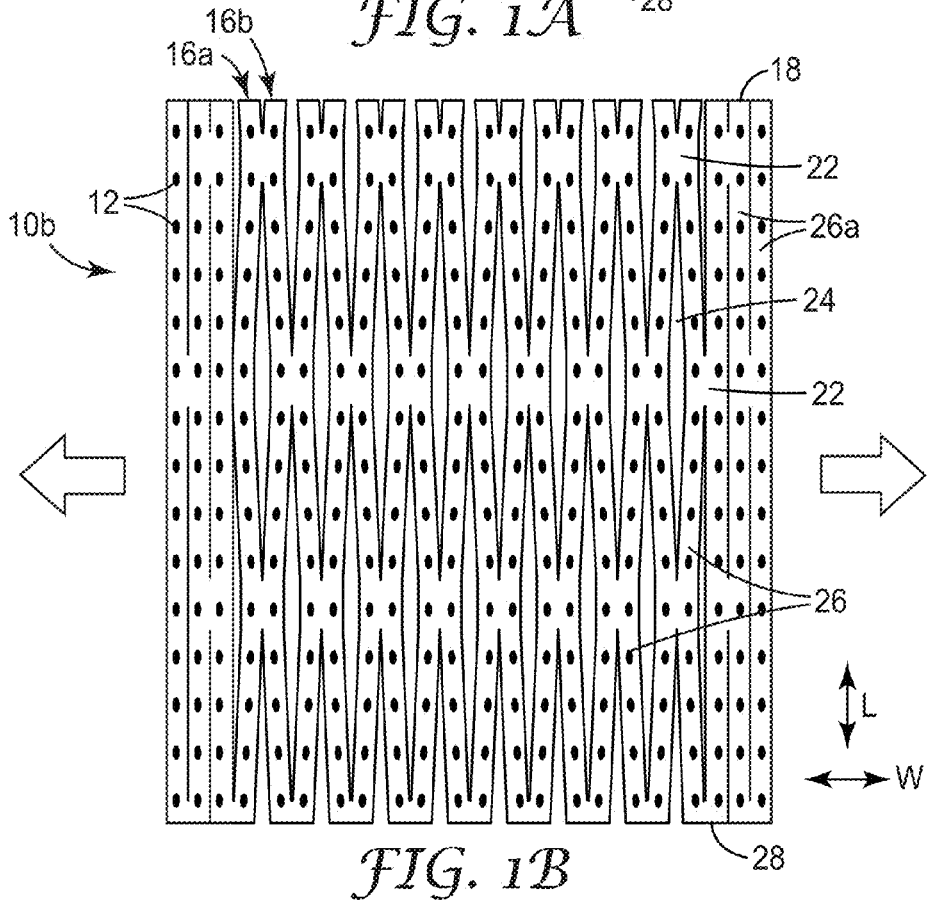
FIG. 1B is a top view of the backing of FIG. 1A after it is spread to provide openings.
Figure 1C:
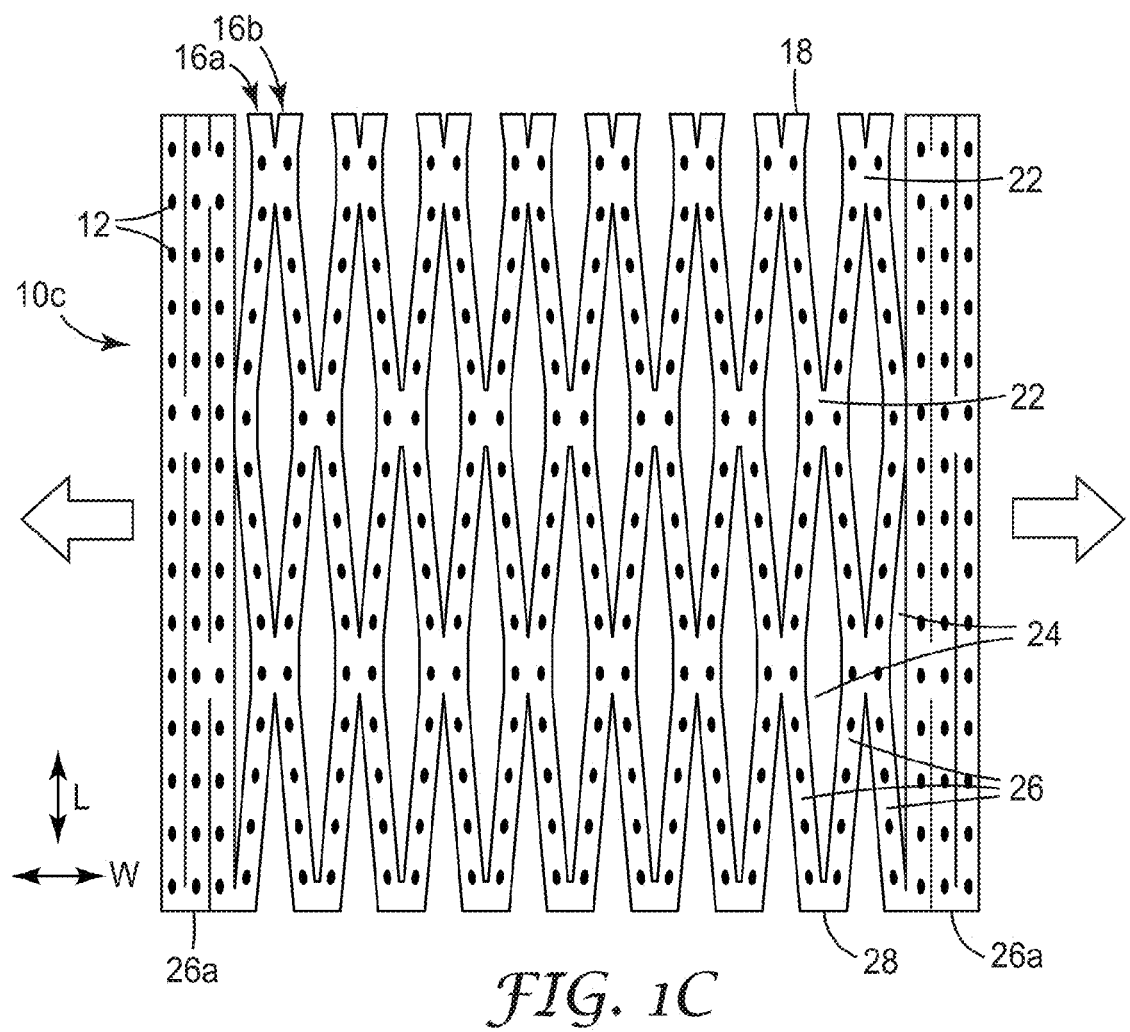
FIG. 1C is a top view of the backing of FIG. 1A after it is spread to a greater extent than in FIG. 1B.

FIGS. 1B and 1C illustrate the effect of spreading the slit backing 10a shown in FIG. 1A to different extents and also illustrate a reticulated mechanical fastening strip 10b, 10c according to the present disclosure. When the slit backing 10a is spread in the direction of the arrows shown, multiple strands 26 of the backing are provided, and the separation between at least some of the multiple strands creates openings 24. Spreading can be carried out to increase the width W of the slit backing (that is, the dimension in the direction of the spreading) to any extent desired. Increasing the width W of the slit backing at least 5 percent may be sufficient to provide openings between the multiple strands. In some embodiments, the width W of the slit backing is increased at least 10, 15, 20, 25, 30, 40, or 50 percent.

Spreading may be carried out to provide openings between all of the multiple strands 26, or spreading may be carried out so that not all of the multiple strands are spread between the bridging regions 22. In FIGS. 1B and 1C, at least two strands 26a, including at least two rows of posts, on each edge of the mechanical fastening strip are not separated. This may be advantageous in some embodiments, for example, to provide a reticulated mechanical fastening strip with a straight edge.

In the reticulated mechanical fastening strip illustrated in FIGS. 1B and 1C, the plurality of upstanding posts 12 on a first strand 26 are arranged in a series 16a that is non-parallel to a series 16b of upstanding posts 12 on a second, adjacent strand 26. The series 16a and 16b of multiple upstanding posts and the multiple strands themselves from which they project can undulate or zig-zag along the length of the reticulated mechanical fastening strip, for example, from the top edge 18 to the bottom edge 28. In the illustrated embodiment, the caps on the posts 12 have an oval shape, and these caps are oriented in different directions along the multiple strands 26 in the longitudinal direction L. When the caps are circular in shape, it may not be observed that the caps are oriented in different directions along the multiple strands 26, unless the cap is marked in some way. In the illustrated embodiment, the caps on a first strand 26 are oriented in a different direction than the caps on a second, adjacent strand 26.

Figure 2A:
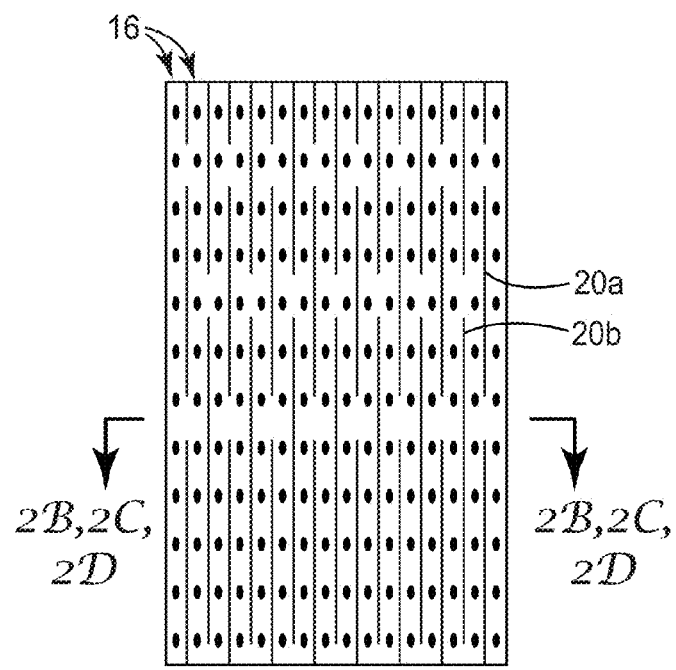
FIG. 2A is a top view of another exemplary backing having upstanding posts and interrupted slits through the backing, useful for the methods of making a mechanical fastening strip disclosed herein.

FIG. 2A illustrates an exemplary slit backing similar to slit backing 10a shown in FIG. 1A. However, in the embodiment shown in FIG. 2A, slit portions 20a have different lengths than slit portions 20b, which results in openings 24a and 24b having different sizes after the slit backing is spread as shown in FIG. 2E. The slit portions of the smaller size 20a and slit portions of the larger size 20b each may be aligned with each other across the backing as shown in FIG. 2A. Or in other embodiments, slits of different sizes may be arranged randomly in the backing or slits of the same size may be offset relative to each other in a regular pattern.

Figure 2B:
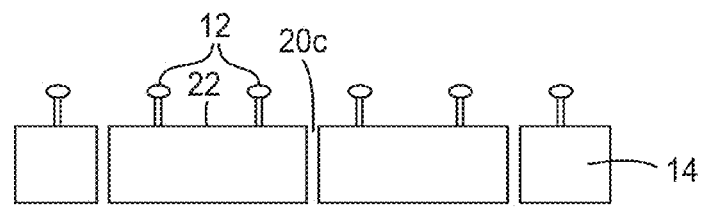
FIG. 2B is a partial, expanded cross-sectional side view taken along line 2BCD-2BCD of FIG. 2A for some embodiments of the methods according to the present disclosure.

A partial, expanded view of an exemplary cross-section taken through the slit backing of FIG. 2A at line 2B, 2C, 2D-2B, 2C, 2D, which extends through some interrupted slits and some bridging regions, is shown in FIG. 2B. In the illustrated embodiment, the interrupted slits 20c cut through the entire thickness of the thermoplastic backing 14. The interrupted slits 20c are made without removing material from the hook strip but are shown out of scale FIG. 2B to make them more easily visible. In other words, the multiple strands of the backing 14 on either side of the interrupted slits 20c are abutting and not spaced apart. The bridging regions 22 of the backing 14 are not slit.

Figure 2C:
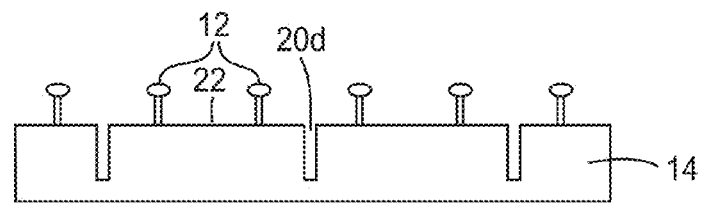
FIG. 2C is a partial, expanded cross-sectional side view taken along line 2BCD-2BCD of FIG. 2A for other embodiments of the methods according to the present disclosure.

The slit backing shown in FIG. 2A can also be made with partial slits as shown in FIG. 2C. In embodiments of FIG. 2A shown in FIG. 2C, partial slits 20d are cut into the first face of the backing 14 (i.e., the same face from which the posts 12 project) between some pairs of adjacent rows 16 of upstanding posts 12. In the illustrated embodiment, the partial slits 20d are interrupted by bridging regions 22 of the backing 14 that are not slit. The partial depth slits penetrate the thickness of the backing to an extent that allows the thermoplastic backing to open during the spreading shown in FIG. 2E. This penetration may be, for example, at least 60, 65, 70, 75, or 80 percent of the thickness of the backing and may be, for example, up to 99, 98, 96, or 95 percent of the thickness of the backing. For example, the penetration may be in a range from 60 to 95, 60 to 90, 65 to 95, 70 to 90, or 65 to 85 percent of the thickness of the backing. Again, in this embodiment, the partial slits 20d are typically made without removing material from the backing 14 but are shown out of scale FIG. 2C to make them more easily visible. Also, like in FIG. 2B, the bridging regions 22 of the backing 14 are not slit.

Figure 2D:
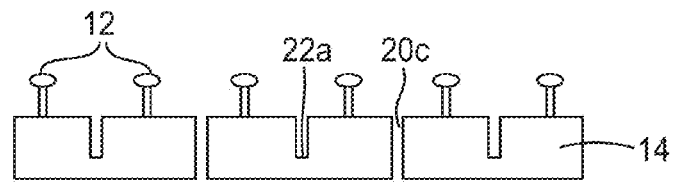
FIG. 2D is a partial, expanded cross-sectional side view taken along line 2BCD-2BCD of FIG. 2A for still other embodiments of the methods according to the present disclosure.
Figure 2E:
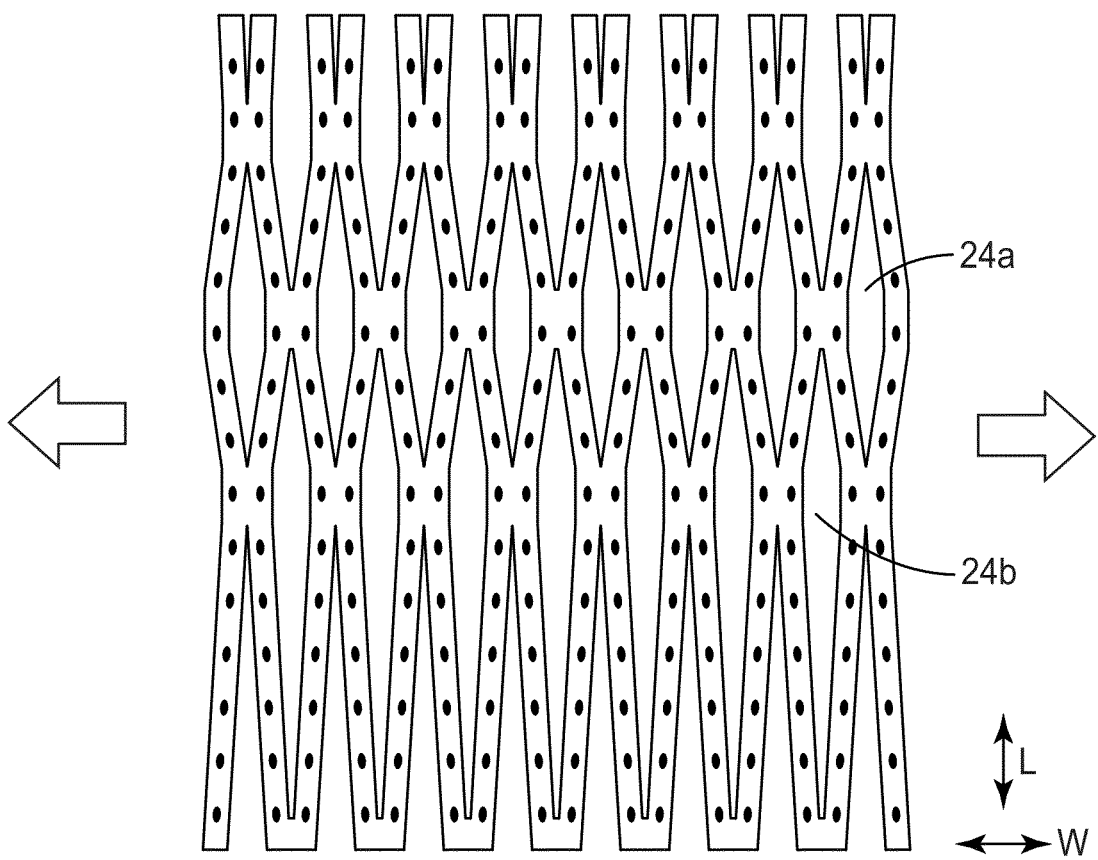
FIG. 2E is a top view of the slit backing of FIG. 2A after it is spread to provide openings.

Another exemplary expanded, partial cross-section taken through the slit backing of FIG. 2A at line 2B, 2C, 2D-2B, 2C, 2D is shown in FIG. 2D. In FIG. 2D, there are partial-depth cuts 22a in the backing 14 in the bridging regions. The partial-depth cuts 22a do not extend through the backing and are collinear with the interrupted slits 20a. The partial depth cuts 22a can penetrate the thickness of the backing to an extent that typically does not allow the thermoplastic backing to easily rupture during the spreading shown in FIG. 2E. For example, the partial-depth cuts 22a may penetrate into the thickness of the backing 14 up to 5, 10, 20, 30, 40, or 50 percent or more. In some embodiments, the partial-depth cuts 22a penetrate the thickness of the backing 14 in a range from 1 to 50, 5 to 40, 10 to 50, 10 to 40, or 25 to 45 percent. The partial-depth cuts 22a may be useful, for example, for providing additional bending flexibility to the mechanical fastening strip.

In the reticulated mechanical fastening strip shown in FIG. 2E, openings 24a and 24b have different sizes. That is, openings 24a are shorter in the longitudinal direction L than openings 24b. It is also possible to make openings that have different widths in a direction W perpendicular to the interrupted slits by using slits of varying lengths. Furthermore, referring again to FIG. 2A, the length of the bridging regions 22 of the backing may be made to vary within a strand 26 or between strands 26 as desired for a particular application or appearance.

Figure 3A:
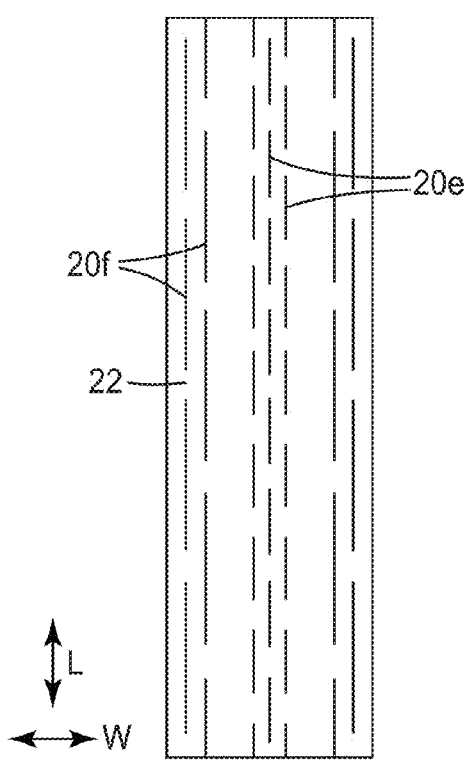
FIG. 3A is a schematic top view of another exemplary backing having upstanding posts and interrupted slits through the backing, useful for the methods of making a mechanical fastening strip disclosed herein.
Figure 3B:
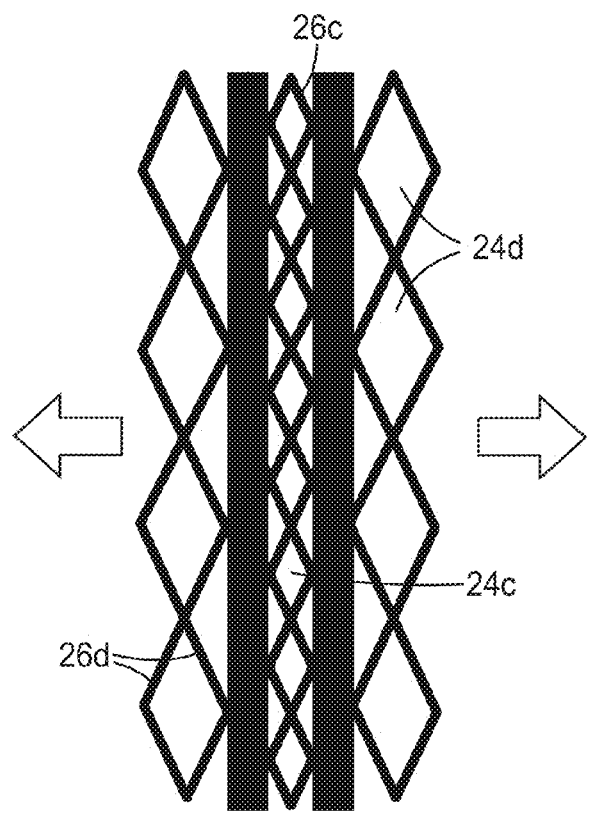
FIG. 3B is a schematic top view of the slit backing of FIG. 3A after it is spread to provide openings.

FIG. 3A illustrates an exemplary slit backing similar to slit backing 10a shown in FIG. 1A. However, in the embodiment shown in FIG. 3A, slit portions 20e have different lengths than slit portions 20f, which results in openings 24c and 24d having different sizes after the slit backing is spread as shown in FIG. 3B. In contrast to the embodiment shown in FIGS. 2A-2E, which illustrates interrupted slits with slit portions of different lengths in the longitudinal direction L, and the corresponding resulting openings, FIGS. 3A and 3B illustrate patterns of slit portions of different lengths in the width direction W. The multiple strands 26c and 26d have a different appearance from each other in the same reticulated mechanical fastening strip, for example, multiple strands 26c and 26d zig-zag or undulate with a different wavelength and amplitude.

Figure 4A:
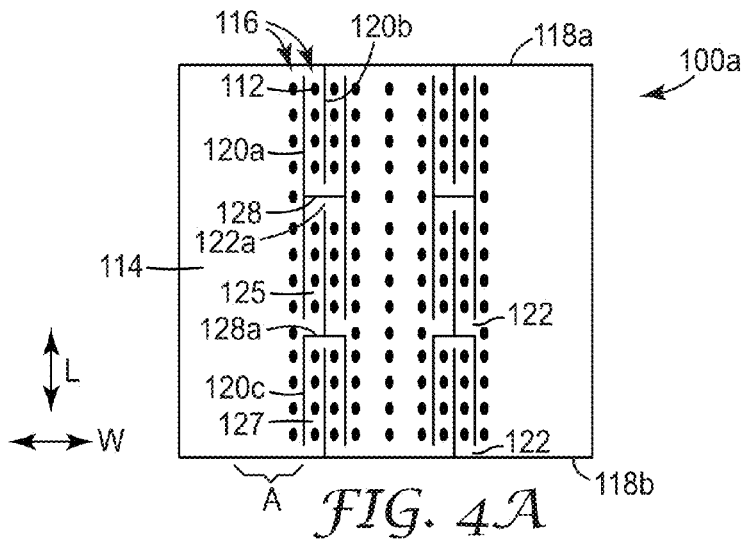
FIG. 4A is a top view of an exemplary backing having upstanding posts and interrupted slits through the backing, useful for the methods of making a mechanical fastening strip disclosed herein.
Figure 4B:
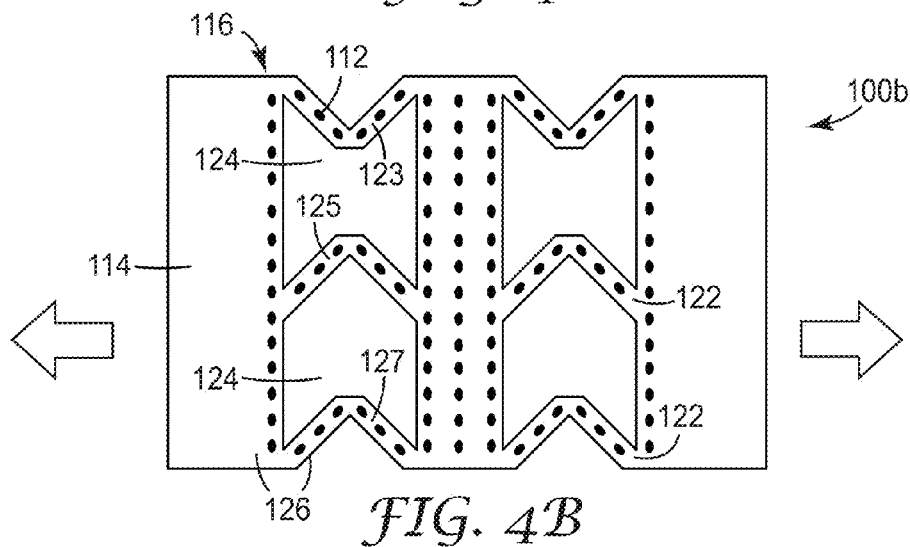
FIG. 4B is a top view of the slit backing of FIG. 4A after it is spread to provide openings.
Figure 4C:
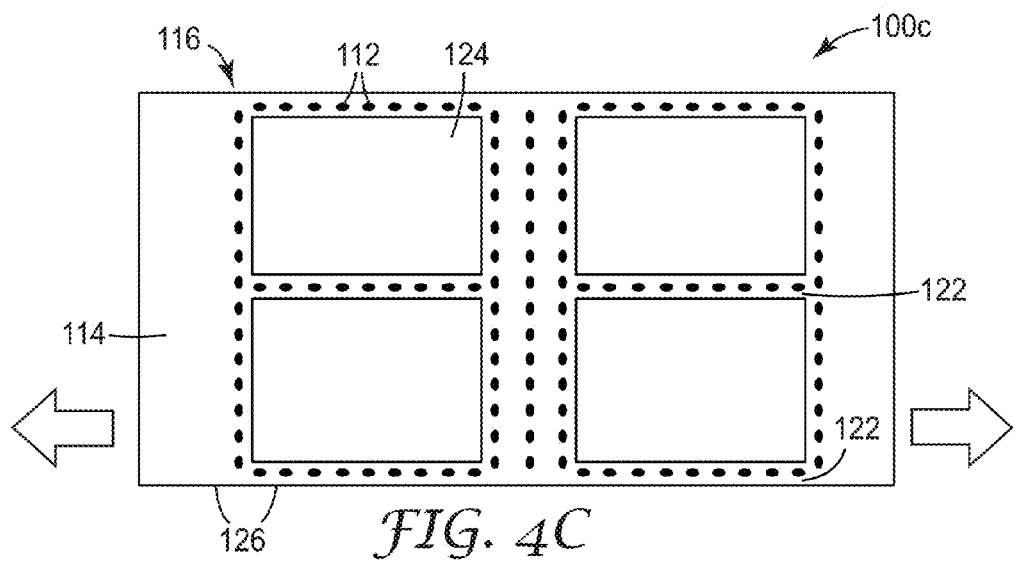
FIG. 4C is a top view of the slit backing of FIG. 4A after it is spread to a greater extent than in FIG. 4B.

FIGS. 4A-4C illustrate another exemplary method for making a mechanical fastening strip and a resulting reticulated mechanical fastening strip according to the present disclosure. In FIG. 4A, slit backing 100a has a thermoplastic backing 114 with multiple rows 116 of upstanding posts 112 projecting from a first surface of the backing 114. The first surface of the backing is the surface that is visible in FIG. 3A. In the illustrated embodiment, the multiple rows 116 of upstanding posts 112 are aligned in the longitudinal direction L. Interrupted slits 120a, 120b, and 120c are cut into the backing between some pairs of adjacent rows 116 of upstanding posts 112. In the illustrated embodiment, a group of three interrupted slits "A" are positioned together to provide connection regions 123, 125, and 127 when the slit web is spread. Each group "A" of three interrupted slits includes a center interrupted slit 120b, which extends through the top and bottom edges 118a and 118b of the backing 114. On either side of the center interrupted slit 120b are interrupted slits that do not extend through the top or bottom edges 118a and 118b of the backing but include a long slit portion 120a and a shorter slit portion 120c. The slit portions of center interrupted slit 120b are relatively shorter than the long slit portion 120a. At least some of the bridging regions 122a of the center interrupted slit 120b are provided with a transverse slit 128, which is transverse to the direction of interrupted slit 120b. In the illustrated embodiment, transverse slit 128 connects long slit portions 120a on either side of the center interrupted slit 120b. Similarly, transverse slit 128a connects the ends of shorter slit portions 120c on either side of center slit 120b. The result of the arrangement of interrupted slit 120b and slit portions 120a and 120c and transverse slits 128 and 128a is the formation of three connection members 123, 125, and 127 surrounding center interrupted slit 120b that allow the slit backing 100a to be spread as shown in FIG. 4B.

FIGS. 4B and 4C illustrate the effect of spreading the slit backing 100a shown in FIG. 4A to different extents and also illustrate a reticulated mechanical fastening strip 100b, 100c according to the present disclosure. When the slit backing 100a is spread in the direction of the arrows shown, multiple strands 126 of the backing are provided, and the separation between at least some of the multiple strands creates openings 124. Furthermore, in the illustrated embodiment, the strands formed from connection members 123, 125, and 127 include portions of two different rows 116 of upstanding posts in the slit backing 100a.

Although the methods of making mechanical fastening strip illustrated in FIGS. 1A-1C, 2A-2E, 3A-3C, and 4A-4C each show interrupted slits extending parallel to the longitudinal direction of the mechanical fastening strip, interrupted slits may be made in any desired direction. For example, interrupted slits may be made at an angle from 1 to 90 degrees to the longitudinal direction of the mechanical fastening strip. When the methods disclosed herein are practiced on a continuous thermoplastic web, interrupted slits may be made in the machine direction, the cross-direction, or any desired angle in between the machine direction and the cross-direction. In some embodiments, interrupted slits in the backing may be made at an angle in a range from 35 to 55 degrees (e.g., 45 degrees) to the longitudinal direction of the mechanical fastening strip.

For the embodiments of reticulated mechanical fastening strips or methods of making them illustrated in FIGS. 1A-1C, 2A-2E, 3A-3C, and 4A-4C, the bridging regions 22 and 122 are staggered in a direction "W" perpendicular to the direction "L" of the interrupted slits 20a-e and 120a-c. For example, referring again to FIG. 1A, the bridging regions 22a and 22b are substantially evenly spaced apart in the direction "L" but are staggered in the direction "W", perpendicular to the direction "L". When the bridging regions are staggered in this manner, the number of bridging regions necessary to make the slit backing handle as an integral unit can be minimized. In other embodiments, the bridging regions 22 and 122 are aligned in a direction "W" perpendicular to the direction of the interrupted slits 20a-e and 120a-c.

The particular arrangement of the bridging regions, whether aligned or staggered in a direction perpendicular to the interrupted slits 20a-e and 120a-c, can be designed, for example, based on the desired length of the slits and the amount of spreading desired for the multiple strands 26, 126. Various lengths of bridging regions 22 and 122 may be useful. In some embodiments, any bridging regions 22 and 122 in a given interrupted slit 20a-g and 120a-c have a combined length in the direction of the interrupted slit of up to 50 (in some embodiments, 40, 30, 25, 20, 15, or 10) percent of the length of the backing in the first direction. In some embodiments, for maximizing the ability of the slit backing 10a and 100a to spread, it may be desirable to minimize the combined length of the bridging regions in the direction of the interrupted slit. Minimizing the combined length of the bridging regions 22 and 122 in the direction of the interrupted slit may be accomplished by at least one of minimizing the length of any particular bridging region 22 and 122 or maximizing the distance between bridging regions 22 and 122. In some embodiments, the length of one bridging region in the direction of the interrupted slit is up to 3, 2, or 1.5 mm and at least 0.25, 0.5, or 0.75 mm. In some embodiments, the number of bridging regions along the length of the mechanical fastening strip 10a-c and 100a-c in the direction of the interrupted slit is up to 1.5, 1.25, 1.0, 0.75, 0.60, or 0.5 per cm. The distance between bridging regions 22 and 122 in the direction of the interrupted slit may be, for example, at least 0.75, 1.0, 1.25, 1.5, or 1.75 cm. Furthermore, the length of the interrupted slit portions between bridging regions can be adjusted and may be selected to maximize the distance between bridging regions. In some embodiments, the length of the interrupted slit portion between bridging regions is at least 8 (in some embodiments, at least 10, 12, 14, 15, 16, 17, 18, 19, or 20) mm. Typically, the interrupted slits of the slit backings disclosed herein have longer slit regions and shorter bridging regions than perforations that are designed to allow easy separation of two parts of a film. For the embodiments of reticulated mechanical fastening strips or methods of making them illustrated in FIGS. 1A-1C, 2A-2E, 3A-3C, and 4A-C, the upstanding posts 12 and 112 in the slit backings 10a and 100a are shown in rows 16 and 116 aligned in the direction of the interrupted slits. However, in some embodiments, the upstanding posts 12 and 112 may be positioned in other arrangements or arranged randomly on the backing 14 and 114. Multiple rows 16 and 116 of upstanding posts 12 and 112 may be evenly spaced or unevenly spaced as desired. For multiple rows 16 and 116 that are evenly spaced, the spacing (e.g., distance in the direction "W") between multiple rows 16 and 116 may differ by up to 10, 5, 2.5, or 1 percent.

For any of the embodiments of reticulated mechanical fastening strips and methods of making a mechanical fastening strip disclosed herein, the number of interrupted slits and resulting openings may be adjusted depending on the requirements of the application. In some embodiments, there are up to 10, 9, 8, 7, 6, 5, 4, 3, 2, or 1 interrupted slits per 10 mm across the width of the backing (i.e., in a direction "W" substantially perpendicular to the first direction or machine direction). In embodiments where the upstanding posts are arranged in rows, changing the number of interrupted slits across the backing is related to the number of rows of upstanding posts between any two adjacent interrupted slits, depending on the density of the upstanding posts on the backing. In some embodiments, the density of upstanding posts 12 on the backing 14 is in a range from 20 per $cm^2$ to 1000 per $cm^2$ (in some embodiments, in a range from 20 per $cm^2$ to 500 per $cm^2$, 50 per $cm^2$ to 500 per $cm^2$, 60 per $cm^2$ to 400 per $cm^2$, 75 per $cm^2$ to 350 per $cm^2$, or 100 per $cm^2$ to 300 per $cm^2$). The number of rows of upstanding post between any two adjacent interrupted slits may be adjusted depending on the requirements of the application. In some embodiments, there are up to 10, 9, 8, 7, 6, 5, 4, 3, 2, or 1 rows of upstanding posts between any two adjacent interrupted slits. In some embodiments, there is an interrupted slit between every other row of upstanding posts.

Various shapes of hook elements may be useful for practicing the present disclosure. In some embodiments, all of the upstanding posts have loop-engaging overhangs (e.g., at the cap). In some of these embodiments, at least a portion of each loop-engaging overhang extends at a nonzero angle to the direction of the interrupted slits (in some embodiments, the machine direction). The nonzero angle may be in a range from 30 to 90 degrees, 50 to 90 degrees, 60 to 90 degrees, 75 to 90 degrees, 80 to 90 degrees, or 85 to 90 degrees. Similarly, in some embodiments of an absorbent article disclosed herein, at least a portion of each of the loop-engaging overhangs may be directed toward the longitudinal center line of the absorbent article when the absorbent article is fastened around the body.

In other embodiments, loop-engaging overhangs (e.g., at the cap) on the upstanding posts of the slit backing extend parallel to the direction of the interrupted slits (in some embodiments, the machine direction). For example, the upstanding posts may have the shape of a J (e.g., as shown in U.S. Pat. No. 5,953,797 (Provost et al.). In some these embodiments, the loop-engaging overhangs extend only in the direction of the interrupted slits (e.g., in some embodiments, the machine direction). In such embodiments, spreading the slit backing typically results in the loop-engaging overhangs oriented in different directions along the multiple strands in the longitudinal direction L as shown in FIGS. 1B, 1C, 2E, 4B, 4C, 5A, and 5B. When loop-engaging overhangs are oriented in multiple directions (e.g., not only one direction such as the machine direction), enhanced engagement of a loop material may advantageously result.

In some embodiments, each upstanding post has a cap with loop engaging overhangs extending in multiple (i.e., at least two) directions. For example, the upstanding post may be in the shape of a mushroom, a nail, a palm tree, or a T. In some embodiments, the upstanding posts are provided with a mushroom head (e.g., with an oval or round cap distal from the thermoplastic backing).

For any of the embodiments of reticulated mechanical fastening strips and methods of making them disclosed herein, the reticulated mechanical fastening strip may be in the form of a roll, from which reticulated mechanical fastening patches are cut in a size appropriate to the desired application. In this application, the reticulated mechanical fastening strip may also be a patch that has been cut to a desired size. Furthermore, in some embodiments, including any of the embodiments described above in connection with FIGS. 1A-C, 2A-E, 3A-C, and 4A-C, backing 14 has a top edge 18 and a bottom edge 28 and the interrupted slits 20a-g or 120a-c extend from the top edge 18 to the bottom edge 28 of the backing. In other embodiments, slits can be made cross-web, from side edge to side edge.

The bridging regions 22 interrupting the interrupted slits 20a allow the hook strip to be handled as an integral unit, for example, to be handled in roll form and converted as desired. Accordingly, in some embodiments, the multiple strands 26 and 126 are not joined to a carrier, at least when the reticulated mechanical fastening strip is initially formed. When the multiple strands are not joined to a carrier, it may mean that the strands are not laminated (e.g., extrusion laminated), adhered, bonded (e.g., ultrasonic bonded or compression bonded) or otherwise attached to a carrier (e.g., a substrate, fastening tab, fastening tape, etc.). Since, in some embodiments, the reticulated mechanical fastening strip according to the present disclosure may be made without being joined to a carrier, there is great flexibility in how the hook strip may be converted and subsequently attached to an article to be fastened.

On the other hand, the reticulated mechanical fastening strip according to the present disclosure may be useful in a fastening laminate. The fastening laminate may be a fastening tab comprising the reticulated mechanical fastening strip disclosed herein in any of the aforementioned embodiments, or the fastening laminate may comprise a reticulated mechanical fastening strip joined to the backsheet of an absorbent article. In some embodiments, the fastening laminate is useful for joining the front waist region and the rear waist region of an absorbent article. The fastening laminate may comprise a carrier and a reticulated mechanical fastening strip disclosed herein, wherein the second face of the reticulated mechanical fastening strip (i.e., the face opposite the upstanding posts) is joined to the carrier.

In some embodiments, fixing the multiple strands of the thermoplastic backing in a spread configuration to maintain the at least one opening between the multiple strands of the thermoplastic backing comprises joining the multiple strands to a carrier. The multiple strands or reticulated mechanical fastening strip may be joined to a carrier, for example, by lamination (e.g., extrusion lamination), adhesives (e.g., pressure sensitive adhesives), or other bonding methods (e.g., ultrasonic bonding, compression bonding, or surface bonding).

The carrier may be continuous (i.e., without any through-penetrating holes) or discontinuous (e.g. comprising through-penetrating perforations or pores). The carrier may comprise a variety of suitable materials including woven webs, nonwoven webs (e.g., spunbond webs, spunlaced webs, airlaid webs, meltblown web, and bonded carded webs), textiles, plastic films (e.g., single- or multilayered films, coextruded films, laterally laminated films, or films comprising foam layers), and combinations thereof. In some embodiments, the carrier is a fibrous material (e.g., a woven, nonwoven, or knit material). In some embodiments, the carrier comprises multiple layers of nonwoven materials with, for example, at least one layer of a meltblown nonwoven and at least one layer of a spunbonded nonwoven, or any other suitable combination of nonwoven materials. For example, the carrier may be a spunbond-meltbond-spunbond, spunbond-spunbond, or spunbond-spunbond-spunbond multilayer material. Or, the carrier may be a composite web comprising a nonwoven layer and a dense film layer.

Fibrous materials that provide useful carriers may be made of natural fibers (e.g., wood or cotton fibers), synthetic fibers (e.g., thermoplastic fibers), or a combination of natural and synthetic fibers. Exemplary materials for forming thermoplastic fibers include polyolefins (e.g., polyethylene, polypropylene, polybutylene, ethylene copolymers, propylene copolymers, butylene copolymers, and copolymers and blends of these polymers), polyesters, and polyamides. The fibers may also be multi-component fibers, for example, having a core of one thermoplastic material and a sheath of another thermoplastic material.

Useful carriers may have any suitable basis weight or thickness that is desired for a particular application. For a fibrous carrier, the basis weight may range, e.g., from at least about 20, 30, or 40 grams per square meter, up to about 400, 200, or 100 grams per square meter. The carrier may be up to about 5 mm, about 2 mm, or about 1 mm in thickness and/or at least about 0.1, about 0.2, or about 0.5 mm in thickness.

One or more zones of the carrier may comprise one or more elastically extensible materials extending in at least one direction when a force is applied and returning to approximately their original dimension after the force is removed. However, in some embodiments, at least the portion of the carrier joined to the second face of the backing is not stretchable. In some embodiments, the portion of carrier joined to the second face of the backing will have up to a 10 (in some embodiments, up to 9, 8, 7, 6, or 5) percent elongation in the cross direction in the direction perpendicular to the slits (i.e., the width direction (W).

In some embodiments, the carrier may be extensible but nonelastic. In other words, the carrier may have an elongation of at least 5, 10, 15, 20, 25, 30, 40, or 50 percent but substantially no recovery from the elongation (e.g., up to 10 or 5 percent recovery). In embodiments of the methods disclosed herein, wherein the carrier is extensible but nonelastic, spreading the slit backing to provide multiple strands of the thermoplastic backing may be carried out after the thermoplastic backing is joined to the extensible carrier (e.g., at the second surface of the thermoplastic backing opposite the surface having the upstanding posts). In these embodiments, fixing the multiple strands of the thermoplastic backing in a spread configuration to maintain the at least one opening between the multiple strands of the thermoplastic backing may be carried out simultaneously with spreading the slit backing, and fixing the multiple strands may be accomplished by the carrier maintaining its elongation. The multiple strands on the extensible carrier may further be annealed as described in more detail below. Suitable extensible carriers may include nonwovens (e.g., spunbond, spunbond meltblown spunbond, or carded nonwovens). In some embodiments, the nonwoven may be a high elongation carded nonwoven (e.g., HEC).

Figure 5A:
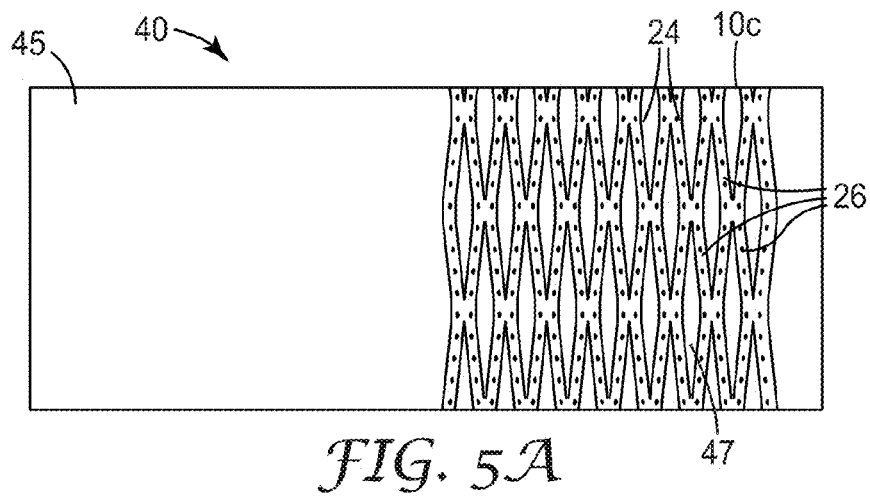
FIG. 5A is a top view of an exemplary fastening laminate according to the present disclosure.
Figure 5B:
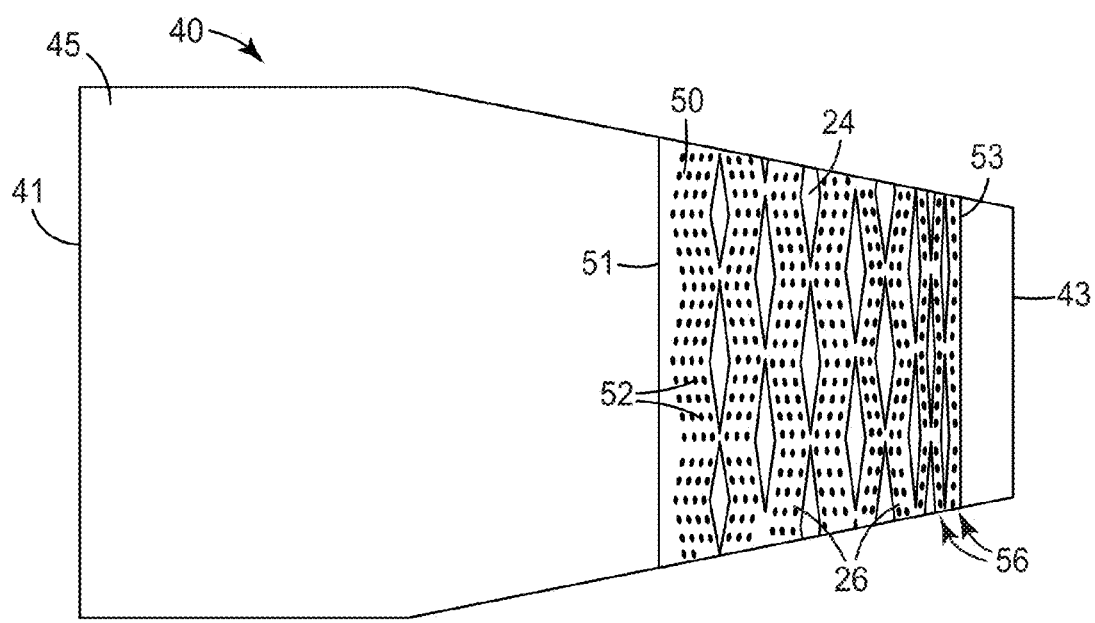
FIG. 5B is a top view of another exemplary fastening laminate according to the present disclosure.

An embodiment of a fastening laminate 40 according to the present disclosure is illustrated in FIG. 5A. Fastening laminate 40 comprises carrier 45 and reticulated mechanical fastening strip 10c, as shown and described in FIG. 1C above. The reticulated mechanical fastening strip includes multiple strands 26 and openings 24 between the strands. Optionally, the fastening laminate 40 can include adhesive 47 between at least a portion of the reticulated mechanical fastening strip and at least a portion of the carrier. In some of these embodiments, there can be exposed adhesive between the multiple strands 26 of the reticulated mechanical fastening strip 10c, which may be advantageous, for example, for allowing the fastening laminate 40 to attach to a surface through a combination of adhesive bonding and mechanical fastening Another fastening laminate 40 according to the present disclosure, comprising carrier 45 and reticulated mechanical fastening strip 10c, is illustrated in FIG. 5B. Fastening laminate 40 may be a fastening tab (e.g., on an absorbent article) with first edge 41 that may be at the manufacturer's end of the fastening tab (i.e., the end that is permanently fixed to the absorbent article, usually in the waist region) and an opposing second edge 43 that may be at the user's end of the fastening tab (i.e., the end that is grasped by the user). In the embodiment illustrated in FIG. 5B, the carrier 45 is shaped such that the second edge 43 is narrower in the longitudinal direction "L" than the first edge 41. The shape of reticulated mechanical fastening strip 50 corresponds to the shape of the carrier 45 with a second edge 53 narrower in the longitudinal direction "L" than a first edge 51. Again second edge 53 of reticulated mechanical fastening strip 50 may be at the user's end of the fastening tab, and first edge 51 may be at the end of the tab permanently attached to the article. In the illustrated embodiment, the width of the multiple strands 26 in reticulated mechanical fastening strip 50 varies, and, therefore, the spacing between openings 24 varies. In some of these embodiments, the number of rows 56 of upstanding posts 12 between openings 24 varies. In fastening laminate 40 shown in FIG. 5B, the strands 26 are thinner toward second edge 53 and larger toward first edge 51. The reticulated mechanical fastening strip in the illustrated embodiment can be made from a slit backing, for example, where there is one row 56 of upstanding posts 52 between adjacent interrupted slits (not shown in FIG. 5B) near the second edge 53 of the slit backing, and the number of rows 56 of upstanding posts 52 increases between adjacent interrupted slits toward the first edge 51 of the slit backing.

The fastening laminates disclosed herein are useful, for example, in absorbent articles. In some embodiments, absorbent articles according to the present disclosure have at least a front waist region, a rear waist region, and a longitudinal center line bisecting the front waist region and the rear waist region, wherein at least one of the front waist region or the rear waist region comprises the fastening laminate disclosed herein. The fastening laminate may be in the form of a fastening tab that is bonded to at least one of the front waist region or the rear waist region extending outwardly from at least one of the left longitudinal edge or the right longitudinal edge of the absorbent article. In other embodiments, the fastening laminate may be an integral ear portion of the absorbent article. In these embodiments, the direction of the slits that provide openings (in some embodiments, the machine direction) of the reticulated mechanical fastening strip is generally aligned with the longitudinal center line of the absorbent article.

Figure 6A:
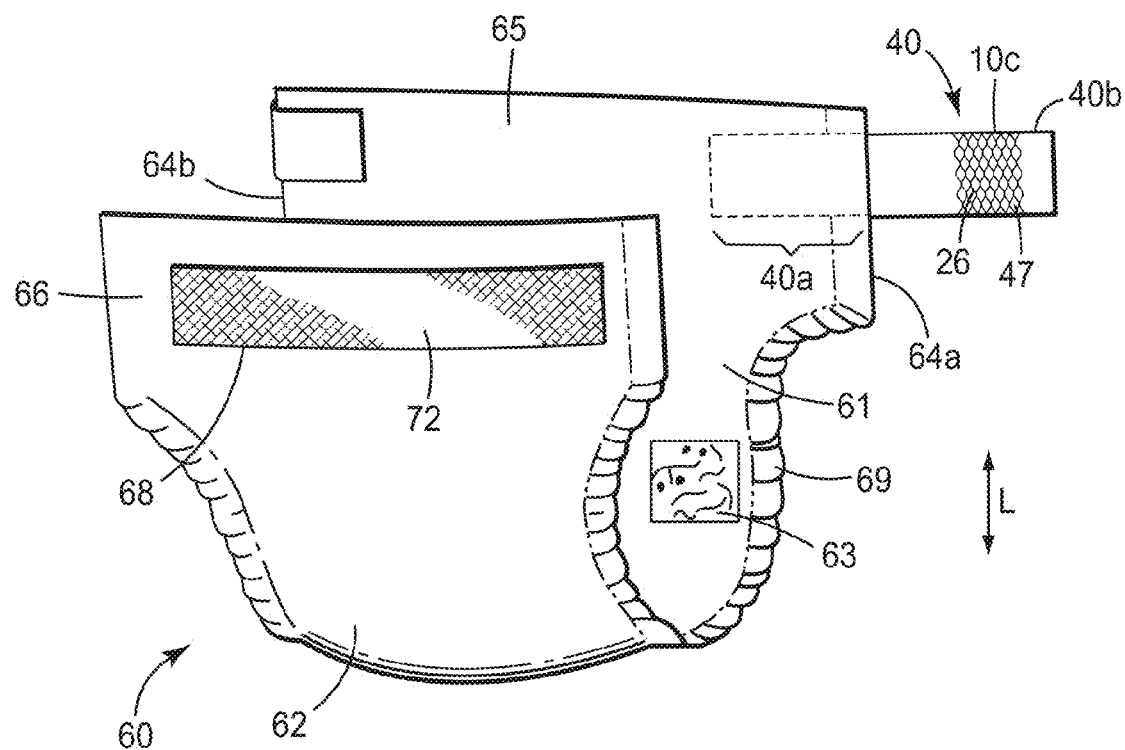
FIG. 6A is a perspective view of an exemplary absorbent article incorporating a mechanical fastening strip according to and/or made according to the present disclosure.

FIG. 6 is a schematic perspective view of one exemplary embodiment of an absorbent article according to the present disclosure. The absorbent article is a diaper 60 having an essentially hourglass shape. The diaper comprises an absorbent core 63 between a liquid permeable top sheet 61 that contacts the wearer's skin and an outwardly facing liquid impermeable back sheet 62. Diaper 60 has a rear waist region 65 having two fastening tabs 40 arranged at the two longitudinal edges 64a, 64b of diaper 60. The diaper 60 may comprise an elastic material 69 along at least a portion of longitudinal side edges 64a and 64b to provide leg cuffs. The longitudinal direction "L" of the absorbent article (e.g., diaper 60) refers to the direction that the article extends from the front to rear of the user. Therefore, the longitudinal direction refers to the length of the absorbent article between the rear waist region 65 and the front waist region 66. The lateral direction of the absorbent article (e.g., diaper 60) refers to the direction that the article extends from the left side to the right side (or vice versa) of the user (i.e., from longitudinal edge 64a to longitudinal edge 64b in the embodiment of FIG. 6).

Fastening tab 40 usually extends beyond longitudinal edges 64a, 64b of the diaper 60. The manufacturer's end 40a corresponds to the part of fastening tab 40 which is fixed or secured to the diaper 60 during the manufacture of the diaper 60. The user's end is typically gripped by the user when attaching the diaper 60 to the wearer and is typically not fixed to the diaper during manufacturing.

In FIG. 6, fastening tabs 40 are secured through their manufacturer's end 40a to the rear waist region 65. The user's end 40b of the fastening tab 40 comprises a reticulated mechanical fastening strip according to the present disclosure. The configuration of reticulated mechanical fastening strip 10c is shown and described above in FIG. 1C. However, the reticulated mechanical fastening strip may also be similar to that shown in any of FIGS. 1B, 2E, 3B, and 4B-4C. In some embodiments, when attaching the diaper 60 to a wearer's body, the user's ends 40b of fastening tabs 40 can be attached to a target area 68 comprising fibrous material 72 which may be arranged on the back sheet 62 of the front waist region 66. Examples of loop tapes which may be applied to the target area 68 to provide an exposed fibrous material 72 are disclosed, for example, in U.S. Pat. No. 5,389,416 (Mody et al.) EP 0,341,993 (Gorman et al.) and EP 0,539,504 (Becker et al.).

In other embodiments, the back sheet 62 comprises a woven or nonwoven fibrous layer which is capable of interacting with the user's ends 40b of fastening tabs 40 comprising a reticulated mechanical fastening strip disclosed herein. Examples of such back sheets 62 are disclosed, for example, in U.S. Pat. No. 6,190,758 (Stopper) and U.S. Pat. No. 6,075,179 (McCormack et al.).

Adhesive 47 can be used to join the reticulated mechanical fastening strip to the carrier 45 and can be used to join the carrier 45 to the rear waist region 65 of the diaper. Exposed adhesive 47 may be present between the multiple strands 26 of reticulated mechanical fastening strip 10c. Fastening tab 40 furthermore optionally comprises release tape (not shown) to contact the exposed part of adhesive 47 when the reticulated mechanical fastening strip 10c is folded onto diaper rear waist region 65 (e.g., during packaging and shipping of diaper 60). The release tape may also be joined to the diaper rear waist region 65 using adhesive. Many configurations of release tape are possible depending on the configuration of the attachment of the fastening tab 40 to diaper 60. The carrier 45 at the user's end of the fastening tab 40 may exceed the extension of the reticulated mechanical fastening strip 10c and the adhesive 47 thereby providing a fingerlift.

During manufacturing or when the diaper 60 is stored prior to use, the user's end of fastening tab 40 is usually folded over onto the top sheet 61 as is shown, for example, for one of the two fastening tabs 40 on the diaper 60 of FIG. 6. It is important during the manufacturing of the diaper 60 that the user's end does not pop open but is releasably secured to the top sheet 61 of the diaper 60. This so-called "anti-flagging feature" of the fastening tab 40 can be provided by the exposed adhesive 47. Furthermore, when the diaper 60 has been used or soiled, it is typically rolled up and discarded, and it is convenient to secure the diaper 60 in the rolled-up state. This so-called "disposal feature" can also provided by the exposed adhesive 47.

Although the embodiment illustrated in FIG. 6 is an absorbent article with attached fastening tabs, it is envisioned that the hook strip disclosed herein would be equally useful in absorbent articles with larger areas of hooks. For example, the ears of the absorbent article themselves comprise hooks, or the absorbent article can have two target zones of loop material along the longitudinal edges of the back sheet in one waist region and two hook strips extending along the longitudinal edges of the absorbent article in the opposite waist region.

In use, fitting an absorbent article such as a diaper about the wearer usually requires the front and back waist portions of the diaper to overlap each other. As the diaper is worn the movements of the wearer tend to cause the overlapping front and back waist portions to shift position relative to each other. In other words, overlapping front and back waist portions are subjected to forces which tend to cause the front and back waist portions to assume a position relative to each other which is different from the position they assume when the diaper is initially fitted to the wearer. Such shifting can be made worse by the forces induced by the elastic at the leg openings. Unless such shifting is limited, the fit and containment characteristics of the diaper are degraded as the diaper is worn. The reticulated mechanical fastening strip according to and/or made according to the present disclosure may provide improved fit and closure stability by resisting such shifting. The resistance to shifting may be enhanced because relatively larger area and flexibility of the reticulated mechanical fastening strip disclosed herein.

Figure 6B:
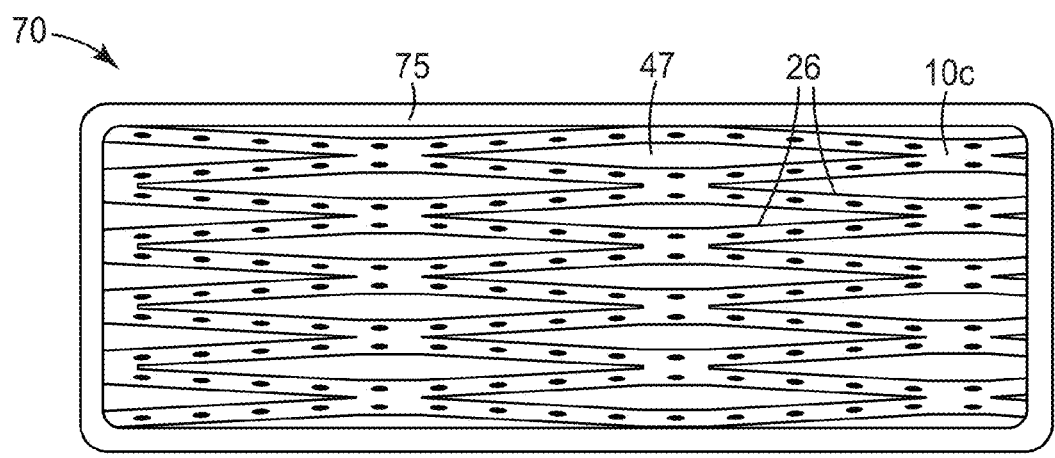
FIG. 6B is a top view of another exemplary absorbent article incorporating a mechanical fastening strip according to and/or made according to the present disclosure.

The fastening laminate may also be useful, for example, for disposable articles such as sanitary napkins. A schematic representation of a sanitary napkin 70 is shown in FIG. 6B. A sanitary napkin typically includes a back sheet 75 that is intended to be placed adjacent to the wearer's undergarment. Reticulated mechanical fastening strip 10c can be attached to the back sheet 75 to fasten the sanitary napkin 70 to an undergarment. The configuration of reticulated mechanical fastening strip 10c is shown and described above in FIG. 1C. However, the reticulated mechanical fastening strip may also be similar to that shown in any of FIGS. 1B, 2E, 3B, and 4B-4C. Adhesive 47 can be used to join the reticulated mechanical fastening strip to the back sheet 75. Exposed adhesive 47 may be present between the multiple strands 26 of reticulated mechanical fastening strip 10c to provide a combination of mechanical and adhesive fastening.

The mechanical fastening strips according to and/or made according to the present disclosure may also be useful in many other fastening applications, for example, assembly of automotive parts or any other application in which releasable attachment may be desirable.

The mechanical fastening strips (e.g., slit backings or reticulated mechanical fastening strips) according to and/or useful for practicing the present disclosure are typically made of a thermoplastic material. Suitable thermoplastic materials mechanical fastening strips include polyolefin homopolymers such as polyethylene and polypropylene, copolymers of ethylene, propylene and/or butylene; copolymers containing ethylene such as ethylene vinyl acetate and ethylene acrylic acid; polyesters such as poly(ethylene terephthalate), polyethylene butyrate and polyethylene napthalate; polyamides such as poly(hexamethylene adipamide); polyurethanes; polycarbonates; poly(vinyl alcohol); ketones such as polyetheretherketone; polyphenylene sulfide; and mixtures thereof. Typically, the thermoplastic is a polyolefin (e.g., polyethylene, polypropylene, polybutylene, ethylene copolymers, propylene copolymers, butylene copolymers, and copolymers and blends of these materials).

In the reticulated mechanical fastening strips disclosed herein and their slit backing precursors, the backing and the upstanding posts are typically integral (that is, formed at the same time as a unit, unitary). Upstanding posts on a backing can be made, for example, by feeding a thermoplastic material onto a continuously moving mold surface with cavities having the inverse shape of the posts. The thermoplastic material can be passed between a nip formed by two rolls or a nip between a die face and roll surface, with at least one of the rolls having the cavities. The cavities may be in the inverse shape of a capped post having a loop-engaging head or may be in the inverse shape of a post without loop-engaging heads (e.g., a precursor to a fastening element). In the methods disclosed herein, the term "posts" is meant to include posts with or without loop-engaging heads, depending on the embodiment. Pressure provided by the nip forces the resin into the cavities. In some embodiments, a vacuum can be used to evacuate the cavities for easier filling of the cavities. The nip is typically sufficiently wide such that a coherent backing is formed over the cavities. The mold surface and cavities can optionally be air or water cooled before stripping the integrally formed backing and upstanding hook elements from the mold surface such as by a stripper roll. If the posts formed upon exiting the cavities do not have loop-engaging heads, loop-engaging heads could be subsequently formed into hooks by a capping method as described in U.S. Pat. No. 5,077,870 (Melbye et al.), the disclosure of which is incorporated herein by reference in its entirety. Typically, the capping method includes deforming the tip portions of the hook elements using heat and/or pressure. The heat and pressure, if both are used, could be applied sequentially or simultaneously.

Other suitable tool rolls include those formed from a series of plates defining a plurality of post-forming cavities about its periphery such as those described, for example, in U.S. Pat. No. 4,775,310 (Fischer). Cavities may be formed in the plates by drilling or photoresist technology, for example. Still other suitable tool rolls may include wire-wrapped rolls, which are disclosed along with their method of manufacturing, for example, in U.S. Pat. No. 6,190,594 (Gorman et al.). Another exemplary method for forming a thermoplastic backing with upstanding posts includes using a flexible mold belt defining an array of upstanding post-shaped cavities as described in U.S. Pat. No. 7,214,334 (Jens et al.). Yet other useful methods for forming a thermoplastic backing with upstanding posts can be found in U.S. Pat. No. 6,287,665 (Hammer), U.S. Pat. No. 7,198,743 (Tuma), and U.S. Pat. No. 6,627,133 (Tuma).

Another useful method for forming upstanding posts (e.g., with loop-engaging heads) on a backing is profile extrusion described, for example, in U.S. Pat. No. 4,894,060 (Nestegard), which is incorporated herein by reference in its entirety. Typically, in this method a thermoplastic flow stream is passed through a patterned die lip (e.g., cut by electron discharge machining) to form a web having downweb ridges, slicing the ridges, and stretching the web to form separated projections. The ridges may form hook precursors and exhibit the cross-sectional shape of upstanding posts (e.g., with loop-engaging heads) to be formed. The ridges are transversely sliced at spaced locations along the extension of the ridges to form discrete portions of the ridges having lengths in the direction of the ridges essentially corresponding to the length of the upstanding posts to be formed. The thermoplastic backing that results from this method has stretch-induced molecular orientation.

In some embodiments, the thermoplastic backing has stretch-induced molecular orientation, for example, when the thermoplastic backing with upstanding posts is prepared by profile extrusion or in other cases where the thermoplastic backing is stretched after formation of the upstanding posts. In other embodiments, the thermoplastic backing is not provided with macroscopic stretch-induced molecular orientation in the direction of the interrupted slits or in the direction of spreading. In these embodiments, there may be some stress-induced orientation localized in the bridging regions.

Some mechanical fastening strips which may be useful precursors for the reticulated mechanical fastening strip according to and/or made according to the present disclosure are commercially available, e.g., from 3M Company, St. Paul, under the trade designations "CS-600" or "CS-1010".

For the reticulated mechanical fastening strip according to the present disclosure in any of its various embodiments or its slit backing precursor, the thickness of the strand or backing may be up to about 400, 250, 150, 100, 75 or 50 micrometers, depending on the desired application. In some embodiments, the thickness of the backing is in a range from 30 to about 225 micrometers, from about 50 to about 200 micrometers, or from about 100 to about 150 micrometers. In some embodiments, the upstanding posts have a maximum height (above the backing) of up to 3 mm, 1.5 mm, 1 mm, or 0.5 mm and, in some embodiments a minimum height of at least 0.05 mm, 0.1 mm, or 0.2 mm. In some embodiments, the upstanding posts have aspect ratio (that is, a ratio of height to width at the widest point) of at least about 2:1, 3:1, or 4:1.

For any of the embodiments of the methods according to the present disclosure, interrupted slits in the backing can be formed, for example, using rotary die cutting of a continuous web having a backing and upstanding posts formed by any of the methods described above. Interrupted slits can be made, for example, by using rotary cutting blades having gaps to form the bridging regions. The height of the blade in the gaps may be adjusted to allow for the bridging regions to be partially cut or not cut at all, depending on the desired embodiment. Other cutting methods (e.g., laser cutting) may also be used. Cutting can be performed from either surface of the continuous web, corresponding to the first surface or second surface of the backing. For bridging regions that have partial-depth cuts, the cuts are typically made in the first surface of the backing, which is the same surface from which the upstanding post project. When the hook elements are formed using the method described above, where a thermoplastic material is fed onto a continuously moving mold surface with cavities having the inverse shape of the upstanding posts, slitting the web and optionally spreading the slit web can be carried out before or after a capping step is carried out to form loop-engaging heads. In some embodiments of the methods disclosed herein, before the thermoplastic backing is slit through and spread, the thermoplastic backing is provided with upstanding posts each have a base attached to the thermoplastic backing and a cap distal from the thermoplastic backing, wherein the cap has a larger area than a cross-sectional area of the base. In other embodiments of the methods disclosed herein, the upstanding posts each have a base attached to the thermoplastic backing and a tip distal from the thermoplastic backing, the method further comprising deforming the distal tip to form a cap. In these embodiments, deforming the distal tip to form a cap can be carried out, for example, after slitting through the backing but before spreading the slit backing; after spreading the slit backing but before fixing the multiple strands of the thermoplastic backing in a spread configuration (in some embodiments, annealing); or after fixing the multiple strands of the thermoplastic backing in a spread configuration as desired.

It should be understood that cutting methods disclosed herein on a continuous web may result in some instances with slits that cross over or cut through a row of upstanding posts. Although the rotary die, for example, may be positioned to form a slit between rows of upstanding posts, the variability in the web process may cause the slit to cross over a row of upstanding posts and later return to its intended position.

For embodiments of reticulated mechanical fastening strips disclosed herein having partial-depth slits, the partial-depth slits may also be made using raised ridges on the roll formed with the cavities having the inverse shape of the upstanding posts to be formed. Or the profiled die lip used in the profile extrusion method can be made to form depressions in the backing. In these embodiments, the slits are formed simultaneously with the upstanding posts during the molding or extrusion process.

In some embodiments of the methods of making a mechanical fastening strip according to the present disclosure, providing a slit backing may be carried out by slitting through the backing in regions of the continuous web to provide interrupted slits while not slitting other regions. Typically, cross-web regions of interrupted slits made in the machine direction alternating with unslit regions may be made. The resulting continuous web may be rolled as a jumbo and stored until further processing. Alternatively, cutting through the unslit regions with a continuous cut (e.g., in the machine direction) can be carried out to provide separate webs of a slit backing, which may be wound individually (e.g., level wound) into rolls and stored for later use.

When the mechanical fastening strip according to and/or made according to the present disclosure is a mechanical fastening patch cut to a desired size, interrupted slits may also be made in the backing by hand, for example, using a razor blade.

For any of the methods of making a mechanical fastening strip according to the present disclosure, spreading the slit backing to provide multiple strands of the thermoplastic backing separated from each other between at least some of the bridging regions to provide at least one opening can be carried out in a variety of suitable ways. For example, spreading can be carried out on a continuous web using a flat film tenter apparatus, diverging rails, diverging disks, or a series of bowed rollers. When spreading is desired in the machine direction of a continuous web (e.g., with interrupted slits are made in the cross-web direction), monoaxial spreading in the machine direction can be performed by propelling the thermoplastic web over rolls of increasing speed, with the down-web roll speed faster than the upweb roll speed. When the mechanical fastening strip according to and/or made according to the present disclosure is a mechanical fastening patch cut to a desired size, spreading the slit backing may also be carried out, for example, by hand.

Figure 1D:
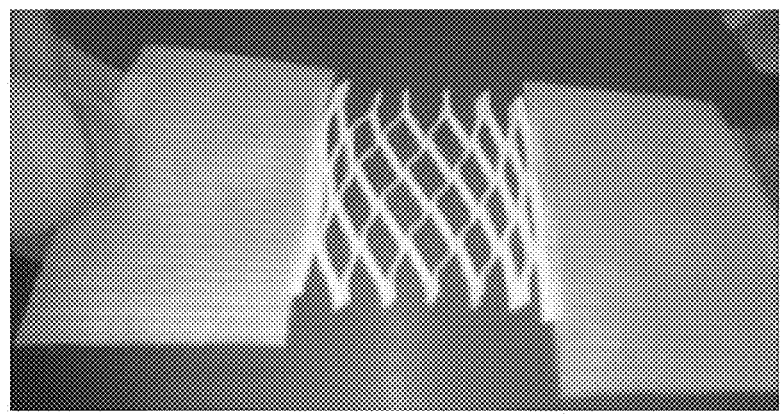
FIG. 1D is a photograph illustrating spreading the mechanical fastening strip in FIG. 1A for some embodiments of the methods disclosed herein.

The slit backing can be considered to be planar, for example, if it is patch cut to a desired size or a web in its unrolled configuration. A result of spreading the slit backing shown in FIG. 1A is shown in the photograph of FIG. 1D. In the photograph of FIG. 1D, pieces of loop material was attached to the edges of a slit backing such as that shown in FIG. 1A. When the pieces of loop material are pulled apart, the individual strands of the backing along with their multiple posts tend to twist out of the plane of the backing as shown in FIG. 1D. The amount of out-of-plane twisting is affected, for example, by the extent to which the slit backing is spread. Furthermore, when the pieces of loop material are released, the multiple strands will typically return to their original positions.

The openings can be maintained between the multiple strands of the backing by joining the multiple strands to a carrier as described above. In other embodiments (e.g., embodiments with a significant extent of spreading), the openings are maintained by annealing the mechanical fastening strip. In some embodiments, annealing comprises heating the mechanical fastening strip. In some embodiments, annealing comprises heating and then cooling (e.g., rapidly cooling) the mechanical fastening strip to maintain its configuration. In some embodiments, heating is only applied to the second surface of the thermoplastic backing (i.e., the surface opposite the first surface from which the upstanding posts project) to minimize any damage to the caps on the upstanding posts that may result from heating.

Heating may be carried out on a continuous web, for example, using heated rollers, IR irradiation, hot air treatment or by performing the spreading in a heat chamber. In embodiments where heated rollers are used, only rollers that are in contact with the second surface of the thermoplastic backing are heated. When the mechanical fastening strip according to and/or made according to the present disclosure is a mechanical fastening patch cut to a desired size, heating the multiple strands of the backing may conveniently be carried out on a hot plate, for example.

The out-of-plane twisting that can be observed when the slit backing is spread (e.g., as shown in FIG. 1D) can be controlled by maintaining or constraining at least some of the multiple strands in a substantially coplanar arrangement. A substantially "coplanar" arrangement refers to the strands occupying substantially the same plane. The term "substantially" in this regard can mean that at least some of the multiple strands can be twisted out of plane by up to 15, 10, or 5 degrees. "At least some" of the multiple strands being constrained refers to at least 25, 50, 75, or 90 percent or more of the multiple strands being constrained. In some embodiments, constraining at least some of the multiple strands is carried out while heating the multiple strands.

Maintaining at least some of the multiple strands in a substantially coplanar arrangement can be carried out, for example, by limiting the extent to which the slit backing is spread. Providing the interrupted slits at an angle to the spreading direction (e.g., a 35 to 55 or 45 degree angle) may maintain at least some of the multiple strands in a substantially coplanar arrangement when the slit backing is spread.

Constraining at least some of the multiple strands in a substantially coplanar arrangement can be carried out, for example, in a narrow gap that does not allow the strands to twist out of plane. In some embodiments, spreading the slit backing is carried out in a narrow gap. In some embodiments, annealing the multiple strands is carried out within a narrow gap. The narrow gap can be formed in a variety of ways. When the mechanical fastening strip according to and/or made according to the present disclosure is a mechanical fastening patch cut to a desired size, the narrow gap can be formed between a hot plate and a cold plate. The second surface of the slit backing (i.e., the surface opposite the upstanding posts) can be placed on the hot plate, and a cold plate can be held against the first surface of the thermoplastic backing with light pressure to press the multiple strands into a substantially coplanar arrangement. Typically, the slit backing can be spread incrementally, pressed between a hot plate and a cold plate, and allowed to cool to maintain the openings between the multiple strands and to constrain the multiple strands in a substantially coplanar arrangement. The process can be repeated until the desired amount of spreading is reached.

Constraining a mechanical fastening strip in a continuous web process can be carried out with a narrow gap between hot and cold surfaces used in connection with the diverging disks or other spreading apparatus described above. It is possible in a continuous web process to incrementally spread the slit backing, for example, with a series of bowed rollers, and anneal by heating and cooling with alternating heated and cooled rollers.

In some embodiments where the carrier is a fibrous web, the joining comprises impinging heated gaseous fluid (e.g., ambient air, dehumidified air, nitrogen, an inert gas, or other gas mixture) onto a first surface of the fibrous web while it is moving; impinging heated fluid onto the second surface of the backing while the continuous web is moving, wherein the second surface is opposite the first surface of the backing; and contacting the first surface of the fibrous web with the second surface of the backing so that the first surface of the fibrous web is melt-bonded (e.g., surface-bonded or bonded with a loft-retaining bond) to the second surface of the backing. Impinging heated gaseous fluid onto the first surface of the fibrous web and impinging heated gaseous fluid on the second surface of the backing may be carried out sequentially or simultaneously.

Melt-bonding (e.g., surface-bonding or loft-retaining bonding) using heated gaseous fluid may be carried out, for example, by passing a fibrous web and the continuous web comprising the backing and the hook elements through a nip formed by two backing rolls. The fibrous web and the continuous web comprising the backing and the hook elements generally are fed into the nip from two different directions and contact each other in the nip. The backing rolls may be arranged so as to operate the nip at very low pressure (e.g., less than about 15 pounds per linear inch (27 Newtons per linear cm), less than about 10 pli (18 Nlc), or less than about 5 pli (9 Nlc)) in comparison to the pressures normally used in the lamination of materials (for which relatively high pressure is often preferred). In some embodiments, at least one of the backing rolls may comprise at least a surface layer of a relatively soft material (e.g., a rubber material with a hardness of less than 70 on the Shore A scale). Such a relatively soft surface layer may be achieved, for example, by the use of a roll with a permanently attached soft surface coating, by the use of a removable sleeve of soft material, or by covering the surface of the backing roll with relatively soft and resilient tape. If desired, the surface of one or both backing rolls may be stepped across the face of the roll so as to provide lamination pressure selectively in certain locations. Heated gaseous fluid may be impinged on the two webs, for example, using a nozzle that is placed close to the nip. The nozzle may be configured to have a first fluid delivery outlet and a second fluid delivery outlet that are in diverging relation (e.g., the flow paths from the first and second delivery outlets differ by at least 25 degrees) to deliver heated gaseous fluid to the two different webs. The fluid may be heated by an external heater before being delivered to the nozzle through a supply line. In addition or instead, heating elements may be supplied within the nozzle, or additional heating (e.g., resistance heating or infrared heating) of the nozzle may be applied. In some embodiments, the impinged heated fluid is locally captured by way of at least one first fluid capture inlet that is locally positioned with regard to the first fluid delivery outlet, and at least one second fluid capture inlet that is locally positioned with regard to the second fluid delivery outlet. Joining the continuous web to a fibrous web using this method may be advantageous, for example, for maintaining the shape of the hook elements and without damaging any of the interrupted or partial slits or bridging regions when the continuous web and the carrier are joined together.

Surface-bonding or loft-retaining bonding may be advantageously performed over a large area or areas (herein termed "area-bonding") in contrast to the small-area bonding (often called point-bonding) that is often achieved by ultrasonic bonding or other melt-bonding processes. The large number of surface-bonded fiber portions that may be randomly and/or uniformly present over the bonded area in such area-bonding can collectively provide adequate bond strength for laminate to be handled and to perform satisfactorily in various end uses. In some embodiments, area-bonds occupy at least about 100 square mm, at least about 400 square mm, or at least 1000 square mm.

Further methods and apparatus for joining a continuous web to a fibrous carrier web using heated gaseous fluid may be found in co-pending U.S. patent applications with Ser.

Nos. 12/974,536 and 12/974,329, both filed Dec. 21, 2010, and incorporated herein by reference in their entirety.

SELECTED EMBODIMENTS OF THE DISCLOSURE

In a first embodiment, the present disclosure provides a method of making a mechanical fastening strip, the method comprising:

providing a thermoplastic backing having multiple rows of upstanding posts on a first surface of the thermoplastic backing;

slitting through the thermoplastic backing to provide a slit backing having interrupted slits between at least some pairs of adjacent rows of the upstanding posts, wherein each interrupted slit is interrupted by at least one intact bridging region of the slit backing;

spreading the slit backing to provide multiple strands of the thermoplastic backing attached to each other at least at some of the bridging regions and separated from each other between at least some of the bridging regions to provide at least one opening; and fixing the multiple strands of the thermoplastic backing in a spread configuration to maintain the at least one opening between the multiple strands of the thermoplastic backing.

In a second embodiment, the present disclosure provides the method of the first embodiment, wherein fixing the multiple strands comprises annealing.

In a third embodiment, the present disclosure provides the method of the first or second embodiment, further comprising maintaining at least some of the multiple strands in a substantially coplanar arrangement.

In a fourth embodiment, the present disclosure provides a method of making a mechanical fastening strip, the method comprising:

providing a thermoplastic backing having upstanding posts on a first surface of the thermoplastic backing;

slitting through the thermoplastic backing to provide a slit backing having interrupted slits, wherein each interrupted slit is interrupted by at least one intact bridging region of the slit backing;

spreading the slit backing to provide multiple strands of the thermoplastic backing attached to each other at least at some of the bridging regions and separated from each other between at least some of the bridging regions to provide at least one opening; and annealing the multiple strands of the thermoplastic backing in a spread configuration to maintain the at least one opening between the multiple strands of the thermoplastic backing.

In the fifth embodiments, the present disclosure provides the method of the second or fourth embodiment, wherein the annealing is carried out while constraining at least some of the multiple strands in a substantially coplanar arrangement.

In a sixth embodiment, the present disclosure provides the method of any one of the first to fifth embodiments, wherein the upstanding posts each have a base attached to the thermoplastic backing and a cap distal from the thermoplastic backing, wherein the cap has a larger area than a cross-sectional area of the base.

In a seventh embodiment, the present disclosure provides the method of any one of the first to fifth embodiments, wherein the upstanding posts each have a base attached to the thermoplastic backing and a tip distal from the thermoplastic backing, the method further comprising deforming the distal tip to form a cap.

In an eighth embodiment, the present disclosure provides the method of any one of the first to seventh embodiments, wherein the multiple rows of upstanding posts are aligned in a machine direction, and wherein the interrupted slits extend in the machine direction.

In a ninth embodiment, the present disclosure provides the method of any one of the first to eighth embodiments, wherein for any two adjacent interrupted slits, the bridging regions are staggered in a direction transverse to the interrupted slits.

In an tenth embodiment, the present disclosure provides the method of any one of the first to ninth embodiments, further comprising providing a transverse slit through at least some of the bridging regions by slitting in a direction transverse to the interrupted slits, such that the transverse slit connects one adjacent interrupted slit on one side of the bridging region to another adjacent interrupted slit on the opposite side of the bridging region.

In an eleventh embodiment, the present disclosure provides the method of any one of the first to tenth embodiments, wherein there is an equal number of rows of upstanding posts between the interrupted slits.

In a twelfth embodiment, the present disclosure provides the method of any one of the first to eleventh embodiments, wherein the interrupted slits cut through the entire thickness of the thermoplastic backing.

In a thirteenth embodiment, the present disclosure provides the method of any one of the first to eleventh embodiments, wherein the interrupted slits are partial-depth slits that allow the thermoplastic backing to open during the spreading.

In an fourteenth embodiment, the present disclosure provides the method of any one of the first to thirteenth embodiments, wherein there are at most tens rows of upstanding posts between any two adjacent interrupted slits.

In a fifteenth embodiment, the present disclosure provides the method of any one of the first to fourteenth embodiments, wherein there are at least two rows of upstanding posts between any two adjacent interrupted slits.

In a sixteenth embodiment, the present disclosure provides the method of any one of the first to fifteenth embodiments, further comprising joining the multiple strands to a carrier.

In a seventeenth embodiment, the present disclosure provides the method of any one of the first to fifteenth embodiments, wherein fixing the multiple strands of the thermoplastic backing in a spread configuration comprises joining the multiple strands to a carrier.

In an eighteenth embodiment, the present disclosure provides the method of the sixteenth or seventeenth embodiment, further comprising applying adhesive to at least one of the carrier, the thermoplastic backing before it is slit, or the multiple strands of the thermoplastic backing.

In a nineteenth embodiment, the present disclosure provides the method of the sixteenth or seventeenth embodiment, wherein the carrier is fibrous, and the second surface of the backing is surface-bonded to the carrier.

In a twentieth embodiment, the present disclosure provides the method of any one of the first to thirteenth embodiments, wherein the multiple strands are not joined to a carrier.

In a twenty-first embodiment, the present disclosure provides the method of any one of the first to twentieth embodiments, wherein there are interrupted slits cut through the backing between at least three pairs of adjacent rows of the upstanding posts, and the number of rows of upstanding posts between at least some of the interrupted slits varies.

In a twenty-second embodiment, the present disclosure provides the method of any one of the first to twenty-first embodiments, any bridging regions of the backing for a given interrupted slit have a combined length in the direction of the interrupted slit of up to fifteen percent of the length of the backing in the direction of the interrupted slit.

In a twenty-third embodiment, the present disclosure provides a reticulated mechanical fastening strip comprising:

multiple strands of a thermoplastic backing attached to each other at bridging regions in the thermoplastic backing and separated from each other between the bridging regions to provide openings in the reticulated mechanical fastening strip, each of the multiple strands having a longitudinal dimension, a width dimension, and a thickness; and a plurality of upstanding posts on each of the multiple strands, the upstanding posts having bases attached to the thermoplastic backing and caps distal from the thermoplastic backing, wherein the width dimension of each of the multiple strands is wider than at least the bases of the upstanding posts.

In a twenty-fourth embodiment, the present disclosure provides the reticulated mechanical fastening strip of the twenty-third embodiment, wherein the plurality of upstanding posts on a first strand are arranged in a series that is non-parallel to a series of upstanding posts on a second, adjacent strand.

In a twenty-fifth embodiment, the present disclosure provides the reticulated mechanical fastening strip of the twenty-fourth embodiment, wherein both the series of upstanding posts and the multiple strands undulate along the length of the reticulated mechanical fastening strip.

In a twenty-sixth embodiment, the present disclosure provides the reticulated mechanical fastening strip of any one of the twenty-third to twenty-fifth embodiments, wherein the caps are oriented in different directions along the multiple strands in the longitudinal direction.

In a twenty-seventh embodiment, the present disclosure provides the reticulated mechanical fastening strip of any one of the twenty-third to twenty-sixth embodiments, wherein the caps on a first strand are oriented in a different direction than the caps on a second, adjacent strand.

In a twenty-eighth embodiment, the present disclosure provides the reticulated mechanical fastening strip of any one of the twenty-third to twenty-seventh embodiments, there are at most ten upstanding posts across the width dimension of the multiple strands.

In a twenty-ninth embodiment, the present disclosure provides the reticulated mechanical fastening strip of any one of the twenty-third to twenty-eighth embodiments, there are at least two upstanding posts across the width dimension of the multiple strands.

In a thirtieth embodiment, the present disclosure provides the reticulated mechanical fastening strip of any one of the twenty-third to twenty-ninth embodiments, wherein the caps have loop-engaging overhangs extending beyond the upstanding posts at a non-zero angle to a longitudinal direction of the multiple strands.

In a thirty-first embodiment, the present disclosure provides the reticulated mechanical fastening strip of any one of the twenty-third to thirtieth embodiments, wherein at least a portion of the multiple strands exhibit stretch-induced molecular orientation in at least one direction (in some embodiments, the longitudinal direction).

In a thirty-second embodiment, the present disclosure provides the reticulated mechanical fastening strip of any one of the twenty-third to thirtieth embodiments, the multiple strands do not exhibit macroscopic stretch-induced molecular orientation in any direction.

In a thirty-third embodiment, the present disclosure provides a fastening laminate comprising a carrier and the reticulated mechanical fastening strip of any one of the twenty-third to thirtieth embodiments joined to the carrier.

In a thirty-fourth embodiment, the present disclosure provides the fastening laminate of the thirty-third embodiment, further comprising adhesive between at least a portion of the reticulated mechanical fastening strip and at least a portion of the carrier. In some of these embodiments, the adhesive is exposed between the multiple strands of the thermoplastic backing.

In a thirty-fifth embodiment, the present disclosure provides the fastening laminate of the thirty-third or thirty-fourth embodiment, wherein the reticulated mechanical fastening strip and the carrier have different colors.

In a thirty-sixth embodiment, the present disclosure provides the fastening laminate of any one of the thirty-third to thirty-fifth embodiments, wherein at least the portion of carrier to the reticulated mechanical fastening strip is joined has up to a ten percent elongation in a second direction perpendicular to the longitudinal direction.

In a thirty-seventh embodiment, the present disclosure provides the fastening laminate of any one of the thirty-third to thirty-sixth embodiments, wherein the fastening laminate has a proximal end (e.g., for permanent attachment to an absorbent article) and a distal end (e.g., for the user to grasp), and the width of the multiple strands increases from the distal end to the proximal end.

In a thirty-eighth embodiment, the present disclosure provides the fastening laminate of any one of the thirty-third to thirty-seventh embodiments, wherein the carrier is fibrous, and the multiple strands are surface-bonded to the carrier.

In thirty-ninth embodiment, the present disclosure provides an absorbent article having at least a front waist region, a rear waist region, and a longitudinal center line bisecting the front waist region and the rear waist region, wherein at least one of the front waist region or the rear waist region comprises a fastening laminate according to any one of the thirty-third to thirty-eighth embodiments.

In fortieth embodiment, the present disclosure provides a sanitary napkin comprising a fastening laminate according to any one of the thirty-third to thirty-eighth embodiments.

This disclosure may take on various modifications and alterations without departing from its spirit and scope. Accordingly, this disclosure is not limited to the above-described embodiments but is to be controlled by the limitations set forth in the following claims and any equivalents thereof. This disclosure may be suitably practiced in the absence of any element not specifically disclosed herein. All patents and patent applications cited above are hereby incorporated by reference into this document in their entirety.

What is claimed is:

1. A reticulated mechanical fastening strip having a longitudinal direction and a width direction, the reticulated mechanical fastening strip comprising:

multiple strands of a thermoplastic backing attached to each other at bridging regions in the thermoplastic backing and separated from each other between the bridging regions to provide openings in the reticulated mechanical fastening strip, each of the multiple strands having a longitudinal dimension, which is the longest dimension of each of the multiple strands, a width dimension, and a thickness; and a plurality of upstanding posts on each of the multiple strands, the upstanding posts having bases attached to the thermoplastic backing and having caps distal from the thermoplastic backing, wherein the width dimension of each of the multiple strands is wider than at least the bases of the upstanding posts, wherein the plurality of upstanding posts on a first strand are arranged in a series that is non-parallel to a series of upstanding posts on a second, adjacent strand, and wherein both the plurality of upstanding posts and the multiple strands undulate along the longitudinal direction of the reticulated mechanical fastening strip.

2. The reticulated mechanical fastening strip of claim 1, wherein the overhangs distal from the thermoplastic backing are comprised in caps, and wherein the caps are oriented in different directions along the multiple strands in the longitudinal direction.

3. The reticulated mechanical fastening strip of claim 1, wherein the overhangs distal from the thermoplastic backing are comprised in caps, and wherein the caps of the upstanding posts in the series on the first strand are oriented in a first set of directions relative to the longitudinal direction, which is different from a second set of directions in which the caps of the upstanding posts in the series on the second, adjacent strand are oriented relative to the longitudinal direction.

4. A fastening laminate comprising a carrier, the reticulated mechanical fastening strip of claim 1 joined to the carrier.

5. The reticulated mechanical fastening strip of claim 1, wherein there are upstanding posts on only one surface of the reticulated mechanical fastening strip.

6. The reticulated mechanical fastening strip of claim 1, wherein there are at least two upstanding posts across the width dimension of at least some of the multiple strands on one surface of the reticulated mechanical fastening strip.

7. The reticulated mechanical fastening strip of claim 1, wherein the overhangs distal from the thermoplastic backing are comprised in caps, and wherein each cap has a larger area than a cross-sectional area of the base.

8. The reticulated mechanical fastening strip of claim 1, wherein at least a portion of the overhangs extend beyond the upstanding posts at a non-zero angle to a direction parallel to the longitudinal dimension of the multiple strands.

9. The reticulated mechanical fastening strip of claim 1, wherein at least a portion of the multiple strands exhibit stretch-induced molecular orientation in at least one direction.

10. The reticulated mechanical fastening strip of claim 1, wherein the multiple strands do not exhibit macroscopic stretch-induced molecular orientation in any direction.

11. The reticulated mechanical fastening strip of claim 1, wherein each of the upstanding posts is in the shape of mushroom, nail, palm tree, a T, or a J.

12. The fastening laminate of claim 4, further comprising adhesive between at least a portion of the reticulated mechanical fastening strip and at least a portion of the carrier.

13. The fastening laminate of claim 12, wherein the adhesive is exposed between at least some of the multiple strands of the thermoplastic backing.

14. The fastening laminate of claim 4, wherein the reticulated mechanical fastening strip and the carrier have different colors.

15. The fastening laminate of claim 4, wherein the fastening laminate has a proximal end and a distal end, and wherein the width of the multiple strands increases from the distal end to the proximal end.

16. The fastening laminate of claim 4, wherein the carrier comprises fibers, and wherein the multiple strands and at least a portion of the fibers of the carrier are surface-bonded.

17. An absorbent article having at least a front waist region, a rear waist region, and a longitudinal center line bisecting the front waist region and the rear waist region, wherein at least one of the front waist region or the rear waist region comprises the fastening laminate of claim 4.

18. A sanitary napkin comprising the fastening laminate of claim 4.

19. The reticulated mechanical fastening strip of claim 1, further comprising multiple strands that are not separated from each other between the bridging regions.

* * * * *